US011833392B2

(12) United States Patent
Eisenhardt et al.

(10) Patent No.: US 11,833,392 B2
(45) Date of Patent: Dec. 5, 2023

(54) METHODS AND SYSTEMS FOR SWIMMING PERFORMANCE ANALYSIS

(71) Applicant: Form Athletica Inc., Vancouver (CA)

(72) Inventors: Dan Eisenhardt, Vancouver (CA); Reynald Hoskinson, Vancouver (CA); Shaghayegh Zihajehzadeh, Vancouver (CA)

(73) Assignee: Form Athletica Inc., Vancouver (CA)

( * ) Notice: Subject to any disclaimer, the term of this patent is extended or adjusted under 35 U.S.C. 154(b) by 1314 days.

(21) Appl. No.: 16/290,771

(22) Filed: Mar. 1, 2019

(65) Prior Publication Data

US 2019/0269968 A1    Sep. 5, 2019

Related U.S. Application Data

(60) Provisional application No. 62/637,976, filed on Mar. 2, 2018.

(51) Int. Cl.
*A63B 24/00* (2006.01)
*A63B 33/00* (2006.01)
(Continued)

(52) U.S. Cl.
CPC ........ *A63B 24/0062* (2013.01); *A61B 5/1121* (2013.01); *A63B 33/004* (2020.08);
(Continued)

(58) Field of Classification Search
CPC . A63B 24/0062; A63B 33/00; A63B 71/0686; A63B 2071/0666;
(Continued)

(56) References Cited

U.S. PATENT DOCUMENTS 5,864,518 A    1/1999  Geiser
2008/0018532 A1*  1/2008  Mackintosh ........... A63B 71/06
                                              342/357.57
(Continued)

OTHER PUBLICATIONS

Tourny-Chollet, C.; Chollet, D.; Hogie, S.; Papparodopoulos, C., "Kinematic analysis of butterfly turns of international and national swimmers", Journal of Sports Sciences, 20:5, 383-390.

(Continued)

*Primary Examiner* — Andrew Schechter
*Assistant Examiner* — Jeremy A Delozier
(74) *Attorney, Agent, or Firm* — DENTONS CANADA LLP

(57) ABSTRACT

Methods for providing swimmers with performance metrics, turn detection, and stroke rate detection are disclosed. An example method comprises mounting a wearable device comprising an accelerometer, gyroscope and processor on a swimmer's head, continuously measuring acceleration using said accelerometer and angular velocity using said gyroscope to provide acceleration and angular velocity signals to said processor, processing said acceleration and angular velocity signals to determine first roll and pitch angles, applying a correction to axes of said gyroscope based on said roll and pitch angles to determine corrected angular velocity signals, initializing a heading angle at a pre-defined, non-zero value, integrating said corrected angular velocity signals over a time window to determine changes to the heading angle, determining maximum and minimum heading angles within the time window, and, recording a turn when a difference between the maximum and minimum heading angles within the time window is at least approximately 180 degrees.

4 Claims, 15 Drawing Sheets

(51) Int. Cl.
A63B 71/06 (2006.01)
A63B 5/11 (2006.01)
A61B 5/11 (2006.01)

(52) U.S. Cl.
CPC ...... *A63B 71/0686* (2013.01); *A61B 2503/10* (2013.01); *A63B 2071/0666* (2013.01); *A63B 2220/40* (2013.01); *A63B 2244/20* (2013.01)

(58) Field of Classification Search
CPC ............ A63B 2220/40; A63B 2244/20; A63B 24/0003; A63B 2220/34; A61B 5/1121; A61B 2503/10; A61B 2562/0219; A61B 5/6803
See application file for complete search history.

(56) References Cited

U.S. PATENT DOCUMENTS

| | | | |
|---|---|---|---|
| 2010/0204952 A1* | 8/2010 | Irlam | A61B 5/681 702/141 |
| 2012/0245714 A1 | 9/2012 | Mueller et al. | |
| 2014/0149066 A1 | 5/2014 | Holopainen et al. | |
| 2016/0084869 A1* | 3/2016 | Yuen | A63B 60/46 73/510 |
| 2017/0046979 A1* | 2/2017 | Lehary | A63B 69/00 |

OTHER PUBLICATIONS

Davey, N.; Anderson, M.; James, D.A., "Validation trial of an accelerometer-based sensor platform for swimming", Sports Technol. 2008, 1, No. 4-5, 202-207.

Vannozzi, G.; Donati, M.; Gatta, G.; Cappozzo, A., "Analysis of swim turning, underwater gliding and stroke resumption phases in top division swimmers using a wearable inertial sensor device", In Biomechanics and Medicine in Swimming XI; Kjendlie, P.L., Stallman, R.K., Cabri, J., Eds; Norwegian School of Sport Sciences: Oslo, Norway, 2010; pp. 178-180.

Siirtola, P.; Laurinen, P.; Roning, J.; Kinnunen, H., "Efficient accelerometer-based swimming exercise tracking", In Proceedings of the 2011 IEEE Symposium on Computational Intelligence and Data Mining (CIDM), Paris, France, Apr. 11-15, 2011; pp. 156-161.

Lee, J.; Leadbetter, R.; Ohgi, Y.; Theil, D.; Burkett, B.; James, D.A., "Quantifying and assessing biomechanical differences in swim turn using wearable sensors", Sports Technol. 2011, 4:3-4, 128-133.

Lee, J.K.; Park, E.J.; Robinovitch, S.N., "Estimation of Attitude and External Acceleration Using Inertial Sensor Measurement During Various Dynamic Conditions", in IEEE Transactions on Instrumentation and Measurement, vol. 61, No. 8, pp. 2262-2273, Aug. 2012.

Slawson, S.E.; Justham, L.M.; Conway, P.P.; Le-Sage, T.; West, A.A., "Characterizing the swimming tumble turn using acceleration data", Proc. Inst. Mech. Eng. Part P: J. Sports Eng. Technol. 2012, 226, 3-15.

Stamm, A.; James, D.A.; Burkett, B.B.; Hagem, R.M.; Thiel, D.V., "Determining maximum push-off velocity in swimming using accelerometers", In Proceedings of the 6th Asia-Pacific Congress on Sports Technology (APCST), Hong Kong, China, Sep. 18-20, 2013, Procedia Engineering 60 (2013), pp. 201-207.

Beanland, E.; Main, L.C.; Aisbett, B.; Gastin, P.; Netto, K., "Validation of GPS and accelerometer technology in swimming", Journal of Science and Medicine in Sport 17 (2014) 234-238.

Mooney, R.; Corley, G.; Godfrey, A.; Quinlan, L.R.; OLaighin, G., "Inertial Sensor Technology for Elite Swimming Performance Analysis: A Systematic Review", Sensors 2016, 16, 18.

* cited by examiner

W1 and W4 are non-turn windows. W2 and W3 are 2 successive turn windows.

METHODS AND SYSTEMS FOR SWIMMING PERFORMANCE ANALYSIS

CROSS REFERENCE TO RELATED APPLICATION

This application claims the benefit of priority of U.S. Provisional Patent Application No. 62/637,976 filed on Mar. 2, 2018, which is hereby incorporated herein by reference in its entirety.

TECHNICAL FIELD

The present disclosure relates to methods and systems for automatic analysis of a swimmer's performance.

BACKGROUND

Turns are a vital aspect of swimming performance and can be used to extract performance parameters such as split time and average velocity per lap. As a result many researchers have used video-based systems to study various turning techniques as discussed for example in reference [1] (cited below). Limited studies have used wearable inertial sensors to detect and investigate swimming turns, where most of them have used back-worn sensors (See references [2, 3, 4, 5]). In these works, a number of turn-specific features have been used for turn detection purposes. Focusing on front crawl flip turn, an accelerometer is used to detect wall push-off and rotation in reference [3]. In this work, the sensor is orientated in a way that X-axis is parallel to the direction of the longitudinal axis in order to be most appropriate for recording the wall-push-off. The Z-axis which is orientated in anterior-posterior direction is used for analyzing the rotation phase during the turn. Using similar accelerometer orientation, a method is proposed in reference [4] which uses both peak detection and zero crossing method to detect the turns based on temporal analysis of different phases of a turn. However, generalizability of the above mentioned methods for swimming strokes other than freestyle is questionable, as discussed for example in reference [6]. In reference [2] a turn detection algorithm is proposed using the angular velocity signal from a triaxial gyroscope. The algorithm is based on peak detection of the signal from the three axis of rotation. However, this approach is very specific to individual turning techniques and is not generalizable to all swimmers. In reference [5] a turn detection algorithm is proposed which is based on integration of acceleration data to detect push-off velocity. However, the integration method is prone to error as highlighted in reference [7].

In other research, a turn detection strategy is proposed in reference [8] in which data from a digital compass and digital accelerometer is processed to determine when the swimmer has changed direction and thereby mark that as a turn. In this method, at the first step acceleration data is used to find the tilt (roll and pitch) angles. Then the estimated tilt angles are used at the second step to correct compass data. At the end, the median filtered corrected compass/and or standard deviation of the compass data is used to detect a turn. Since a big change in heading direction after a turn is a common feature across all type of turns, compared to other existing turn detection methods, this method has the best generalizability.

However, the following error sources might affect the final accuracy of the method of reference [8]:

a. Accelerometer-based tilt angle detection is not accurate especially during highly dynamic activities (see reference [7]) such as swimming. In the accelerometer signal, gravitational acceleration is combined with activity-related acceleration (also called external acceleration). During dynamic activities, external acceleration corrupts the gravitation acceleration, which in turn makes the acceleration-based tilt angle detection inaccurate.

b. When a compass sensor (magnetometer) is used to calculate the heading angle, any change in the magnetic characteristics of the environment may result in error in heading angle estimation. For example, in a swimming pool any electrical equipment inside the wall at both ends of the pool might affect the heading measurements.

Stroke rate is another important kinematic variable in swimming which has been shown to correlate to competition success, as discussed in reference [9]. On day-to-day basis, stroke rate is quantified by manual counting of the number of strokes and the use of stopwatches which may incorporate inconsistencies due to human error. Using wrist-worn devices, some studies have used metallic sensors to detect swim strokes, as discussed in reference [10]. The metallic sensors act as a short circuit when submerged in water to cause an interrupt condition of the internal microprocessor corresponding to a stroke. In another study a stroke counter is proposed which uses changes in pressure proximate the arms and legs of the swimmer to determine when the swimmer performs a swimming stroke using either the arms or legs, as discussed in reference [11].

Wearable IMUs can also be used to measure swimming kinematic variables including stroke rate. The back and wrist are the most prevalent locations for mounting IMUs to measure stroke rate. Stroke rate detection approach for these two IMU mounting locations typically involves the detection and summation of acceleration peaks for a given lap, as discussed in reference [6]. Studies show that a lower back IMU can measure number of strokes with accuracy of about 90% for all strokes except the freestyle for which the accuracy is only 65%, as discussed in reference [12]. On the other hand adding a wrist-worn IMU can improve the accuracy to about 99% for all stroke types, as discussed in reference [13]. Recent attempts to determine stroke count using a head mounted device have also been made, as discussed in reference [9]. Using peak detection method, excellent accuracy was reported for butterfly and breaststroke. However, during freestyle and backstroke, swimmers aim to keep their head as steady as possible, as a result pattern of repeated peaks is not observed which makes stroke rate detection difficult. Additionally, swimmers use different breathing patterns (every stroke, every 2 strokes, etc.) which may not be synchronized with arm motion in each stroke. This causes further complication in stroke rate detection.

The following references, each of which are hereby incorporated in their entirety, are relevant to the present disclosure:

[1] Tourny-Chollet, C.; Chollet, D.; Hogie, S.; Papparodopoulos, C. Kinematic analysis of butterfly turns of international and national swimmers. *J. Sports Sci.* 2002, 20, 383-390.

[2] Vannozzi, G.; Donati, M.; Gatta, G.; Cappozzo, A. Analysis of swim turning, underwater gliding and stroke resumption phase in top division swimmers using a wearable inertial sensor device. In *Biomechanics and Medicine in Swimming XI*; Kjendlie, P. L., Stallman, R. K., Cabri, J., Eds.; Norwegian School of Sport Sciences: Oslo, Norway, 2010; pp. 178-180.

[3] Lee, J. B.; Leadbetter, R. I.; Ohgi, Y.; Theil, D. V.; Burkett, B.; James, D. A. Quantifying and assessing biomechanical differences in swim turn using wearable sensors. *Sports Technol.* 2011, 4, 128-133.

[4] Slawson, S. E.; Justham, L. M.; Conway, P. P.; Le-Sage, T.; West, A. A. Characterizing the swimming tumble turn using acceleration data. *Proc. Inst. Mech. Eng. Part P J. Sports Eng. Technol.* 2012, 226, 3-15.

[5] Stamm, A.; James, D. A.; Burkett, B. B.; Hagem, R. M.; Thiel, D. V. Determining maximum push-off velocity in swimming using accelerometers. In Proceedings of the 6th Asia-Pacific Congress on Sports Technology (APCST), Hong Kong, China, 18-20 Sep. 2013; pp. 201-207.

[6] Mooney, R.; Corley, G.; Godfrey, A.; Quinlan, L. R.; ÓLaighin, G. Inertial Sensor Technology for Elite Swimming Performance Analysis: A Systematic Review. *Sensors* 2016, 16, 18.

[7] J. K. Lee, E. J. Park and S. N. Robinovitch, "Estimation of Attitude and External Acceleration Using Inertial Sensor Measurement During Various Dynamic Conditions," in *IEEE Transactions on Instrumentation and Measurement*, vol. 61, no. 8, pp. 2262-2273, August 2012.

[8] US20120245714 A1, System and method for counting swimming laps, 2009.

[9] Beanland E., Main L C, et. al., "Validation of GPS and accelerometer technology in swimming", J Sci Med Sport. 2014 March; 17(2):234-8. doi: 10.1016/j.jsams.2013.04.007.

[10] Geiser W. G, "Device and Method for Analyzing a Swimmer's Swim Stroke", US Patent US005864518A, January 1999.

[11] Holopainen R. K., et. al. "Swim Stroke Counter", US Patent US20140149066A1, May 2014.

[12] Davey, N.; Anderson, M.; James, D. A. Validation trial of an accelerometer-based sensor platform for swimming. Sports Technol. 2008, 1, 202-207.

[13] Siirtola, P.; Laurinen, P.; Roning, J.; Kinnunen, H. Efficient accelerometer based swimming exercise tracking. In Proceedings of the 2011 IEEE Symposium on Computational Intelligence and Data Mining (CIDM), Paris, France, 11-15 Apr. 2011; pp. 156-161.

The inventors have determined a need for improved methods and systems for swimming performance analysis.

SUMMARY

One aspect provides a method for detection of swimming turns comprising mounting a wearable device comprising an accelerometer, gyroscope and processor on a swimmer's head, continuously measuring acceleration using said accelerometer and angular velocity using said gyroscope to provide acceleration and angular velocity signals to said processor, applying a correction to axes of said gyroscope based on said roll and pitch angles to determine corrected angular velocity signals, initializing a heading angle at a pre-defined, non-zero value, integrating said corrected angular velocity signals over a time window to determine changes to the heading angle, determining a maximum heading angle and a minimum heading angle within the time window, and, recording a turn when a difference between the maximum heading angle and the minimum heading angle within the time window is at least approximately 180 degrees. In some embodiments, processing acceleration and angular velocity signals and integrating comprises using a sensor fusion algorithm.

Another aspect provides a method for detecting stroke rate for freestyle swimming comprising: mounting a wearable device comprising an inertial measurement unit (IMU) and processor on a swimmer's head; continuously measuring head acceleration signals to obtain head roll data; processing the head roll data to determine breath instances; continuously measuring head acceleration signals to obtain head roll angle data; processing the head roll angle data to determine breath instances; when a number of determined breath instances is at least a minimum threshold: calculating candidate stroke rate estimates based on time between breath instances, comparing the candidate stroke rate estimates to upper and lower threshold values to determine selected strode rate estimate, and, calculating an average stroke rate from the selected stroke rate estimates; and, when the number of determined breath instances is lower than the minimum threshold: determining a fast Fourier transform (FFT) of the head roll data, and, processing the head roll angle data to determine an average stroke rate based on a peak value FFT component.

Another aspect provides a method for detecting stroke rate for butterfly and breaststroke swimming comprising: mounting a wearable device comprising an inertial measurement unit (IMU) and processor on a swimmer's head; continuously measuring head acceleration and angular velocity signals to obtain one or more of compensated vertical acceleration data and forward acceleration data; processing the one or more of compensated vertical acceleration data and forward acceleration data to determine breath instances; calculating candidate stroke rate estimates based on time between breath instances; comparing the candidate stroke rate estimates to upper and lower threshold values to determine selected stroke rate estimates; and calculating an average stroke rate from the selected stroke rate estimates.

Another aspect provides a method for detecting stroke rate for backstroke swimming comprising: mounting a wearable device comprising an inertial measurement unit (IMU) and processor on a swimmer's head; continuously measuring head acceleration and angular velocity signals to obtain one or more of forward acceleration data, compensated vertical acceleration data and head roll angle data; determining a fast Fourier Transform (FFT) for each of one or more of forward acceleration data, compensated vertical acceleration data and head roll angle data; selecting a more dominant one of one or more of forward acceleration data, compensated vertical acceleration data and head roll angle data having a lowest average of FFT component values; and processing the more dominant one of the one or more of forward acceleration data, compensated vertical acceleration data and head roll angle data to determine an average stroke rate based on a peak value FFT component.

Another aspect provides a method for providing a swimmer with real time performance metrics comprising: mounting a wearable device comprising a processor and an inertial measurement unit (IMU) comprising an accelerometer and a gyroscope on the swimmer's head; continuously measuring acceleration and angular velocity with the accelerometer and gyroscope to provide acceleration and angular velocity signals to the processor; processing the acceleration and angular velocity signals to determine first roll and pitch angles; applying an axial correction to axes of said gyroscope based on said roll and pitch angles to determine corrected angular velocity signals; initializing a heading angle at a pre-defined, non-zero value; integrating said corrected angular velocity signals over a time window to determine changes to the heading angle; determining a maximum heading angle and a minimum heading angle within the time window; recording a turn when a difference between the maximum heading angle and the minimum heading angle within the time window is at least approximately 180 degrees; automatically detecting a stroke type based on the acceleration and angular velocity signals; when the stroke type is freestyle, continuously measuring head acceleration signals to obtain head roll data; processing the head roll data to determine breath instances; continuously measuring head acceleration signals to obtain head roll angle data; processing the head roll angle data to determine breath instances; when a number of determined breath instances is at least a minimum threshold: calculating candidate stroke rate estimates based on time between breath instances, comparing the candidate stroke rate estimates to upper and lower threshold values to determine selected strode rate estimate, and, calculating an average stroke rate from the selected stroke rate estimates; and, when the number of determined breath instances is lower than the minimum threshold: determining a fast Fourier transform (FFT) of the head roll data, and, processing the head roll angle data to determine an average stroke rate based on a peak value FFT component; when the stroke type is butterfly or breaststroke, continuously measuring head acceleration and angular velocity signals to obtain one or more of compensated vertical acceleration data and forward acceleration data; processing the one or more of compensated vertical acceleration data and forward acceleration data to determine breath instances; calculating candidate stroke rate estimates based on time between breath instances; comparing the candidate stroke rate estimates to upper and lower threshold values to determine selected stroke rate estimates; and calculating an average stroke rate from the selected stroke rate estimates; and when the stroke type is backstroke, continuously measuring head acceleration and angular velocity signals to obtain one or more of forward acceleration data, compensated vertical acceleration data and head roll angle data; determining a fast Fourier Transform (FFT) for each of one or more of forward acceleration data, compensated vertical acceleration data and head roll angle data; selecting a more dominant one of one or more of forward acceleration data, compensated vertical acceleration data and head roll angle data having a lowest average of FFT component values; and processing the more dominant one of the one or more of forward acceleration data, compensated vertical acceleration data and head roll angle data to determine an average stroke rate based on a peak value FFT component; and reporting the average stroke rate to the swimmer.

Further aspects and details of example embodiments are set forth below.

DRAWINGS

The following figures set forth embodiments in which like reference numerals denote like parts. Embodiments are illustrated by way of example and not by way of limitation in the accompanying figures.

Figure 14:
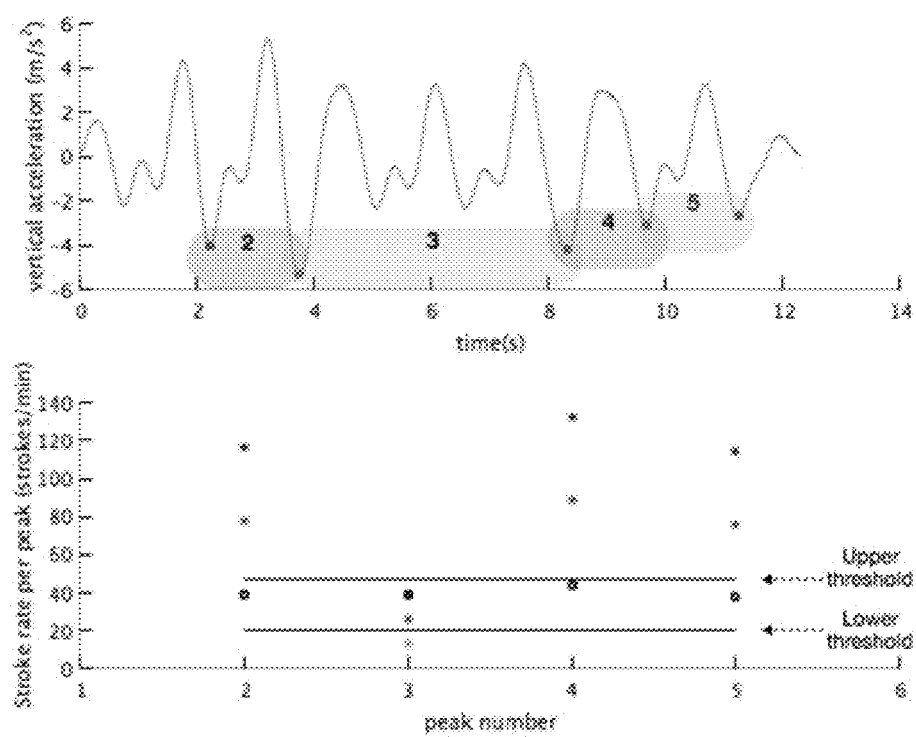

FIG. 14 shows detected peaks of vertical acceleration during 1 full length of butterfly in the top graph, and in the bottom graph shows 3 calculated stroke rates in between each 2 successive breathing instances, with the selected ones shown by back circles.

Figure 15:
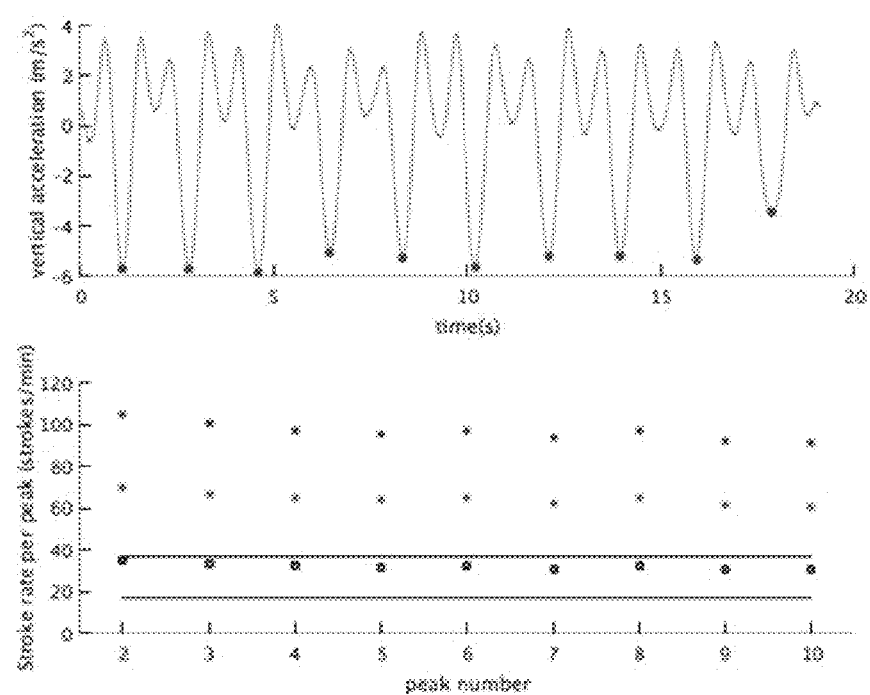

FIG. 15 shows detected peaks of vertical acceleration during 1 full length of breaststroke in the top graph, and in the bottom graph shows 3 calculated stroke rates in between each 2 successive breathing instances, with the selected ones shown by back circles.

Figure 16:
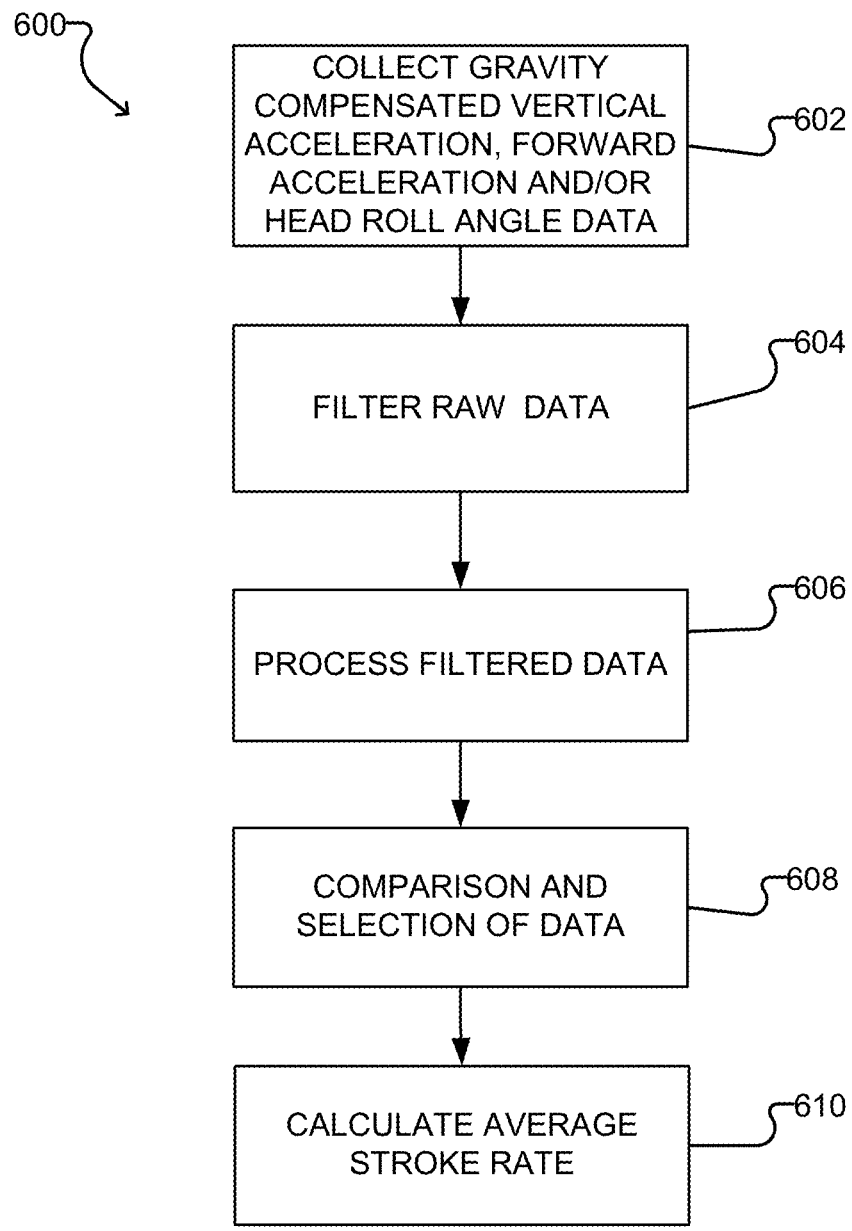

FIG. 16 is a flowchart showing an example method of stroke rate detection for backstroke according to the present disclosure.

Figure 17:
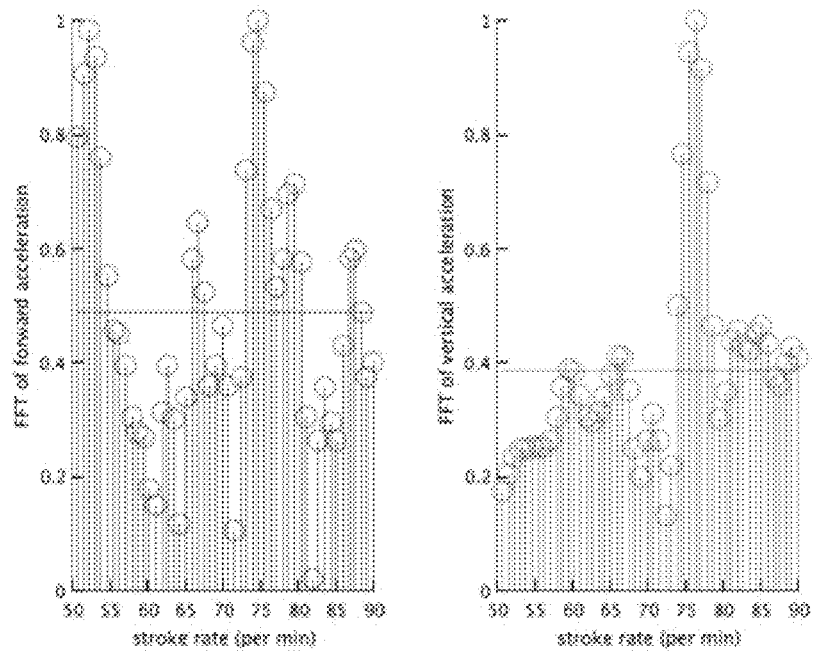

FIG. 17 shows normalized FFT spectrum for a swimmer where the peak of FFT signal is more dominant for the vertical acceleration compared to forward acceleration.

Figure 18:
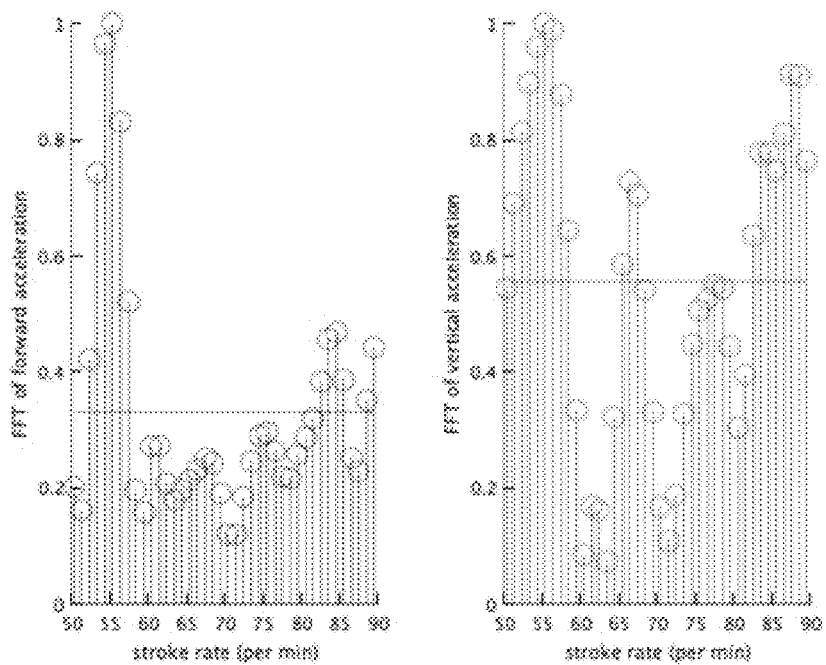

FIG. 18 shows normalized FFT spectrum for a swimmer where the peak of FFT signal is more dominant for the forward acceleration compared to vertical acceleration.

Figure 19:
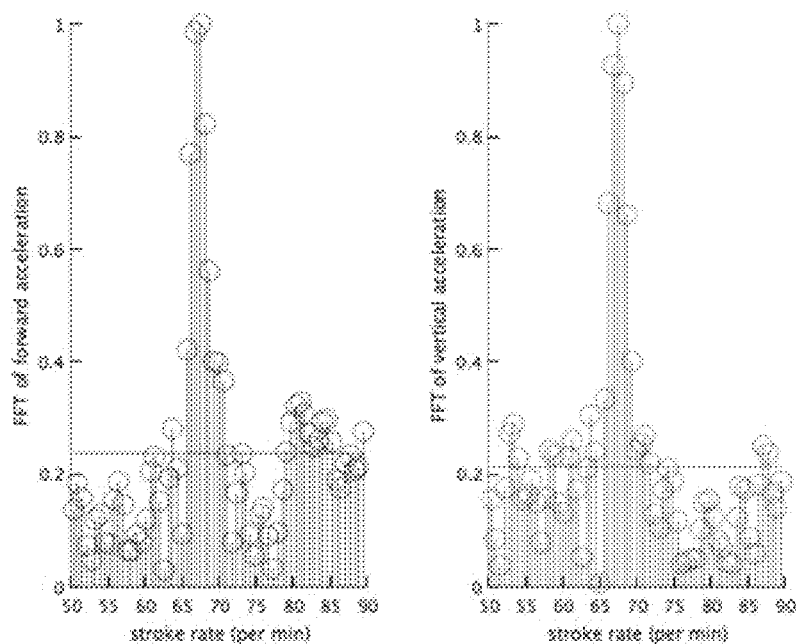

FIG. 19 shows normalized FFT spectrum for a swimmer where the peak of FFT signal has only one dominant peak in both the vertical acceleration and the forward acceleration.

Figure 20:
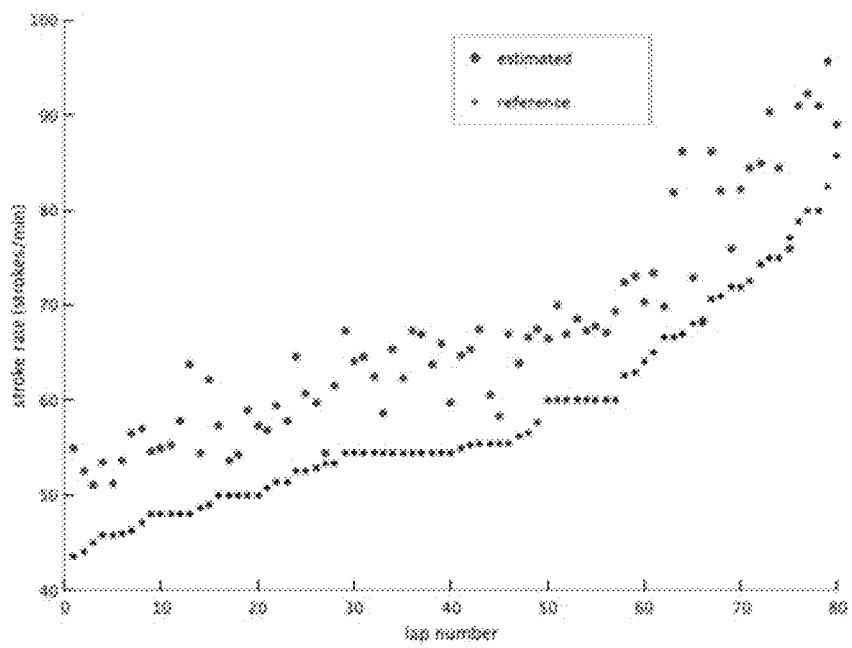

FIG. 20 shows example calculated stroke rate values (red dots) versus reference values (black dots).

Figure 21:
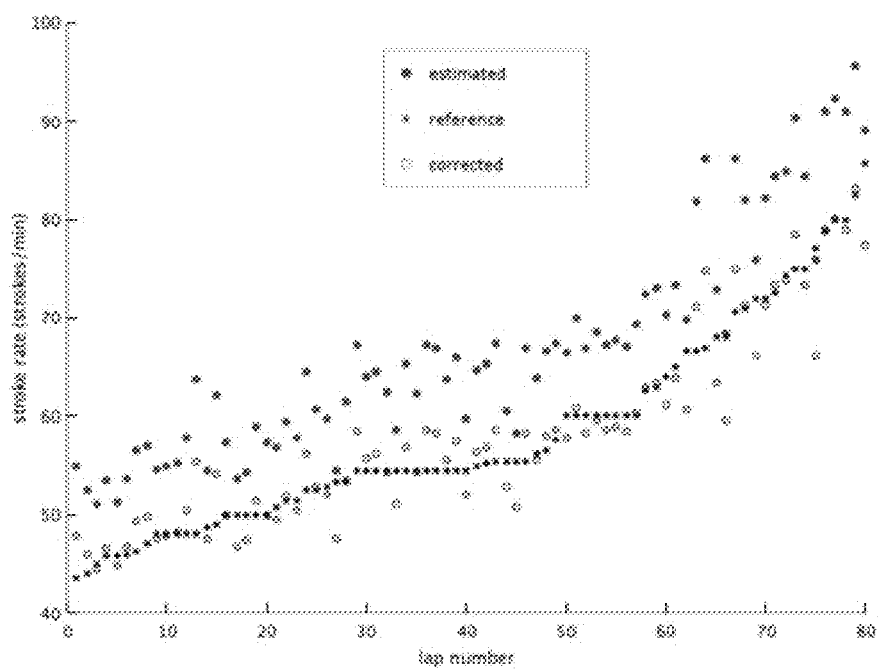

FIG. 21 shows corrected stroke rate values (blue dots) after applying a linear correction.

Figure 22:
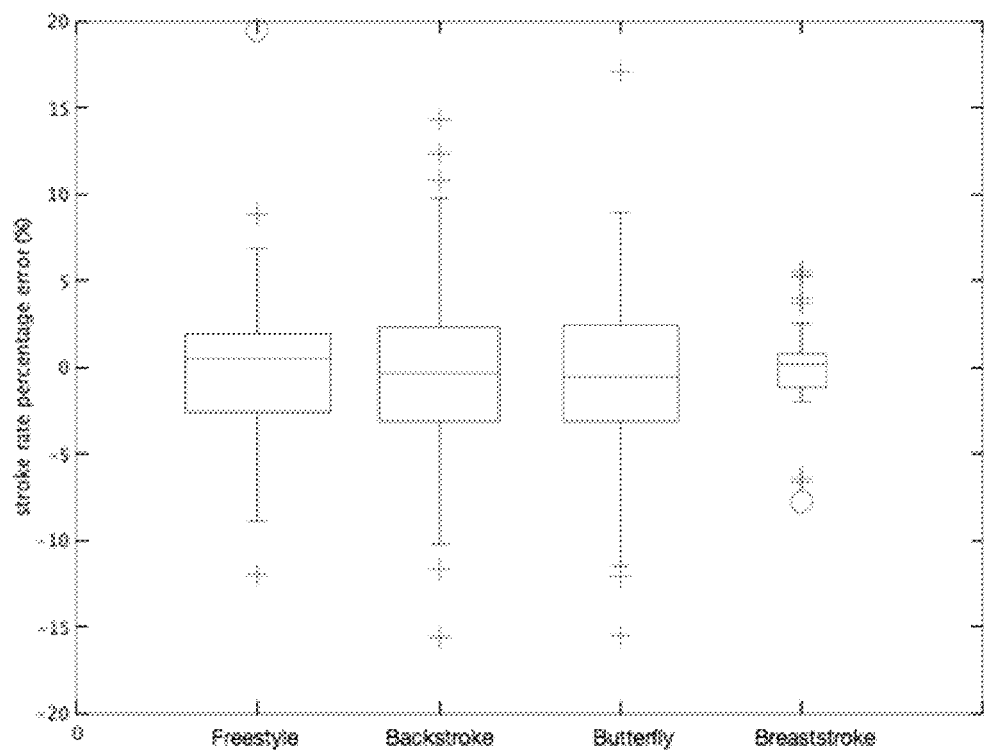

FIG. 22 shows a box plot of errors for each stroke type.

DETAILED DESCRIPTION

The following describes methods and systems for automatic turn and stroke detection in swimming.

Example methods use a triaxial accelerometer and triaxial gyroscope of a wearable inertial measurement unit (IMU) and avoid the use of a magnetometer. The acceleration data from the triaxial accelerometer and angular velocity data from the triaxial gyroscope are used in turn and stroke detection in swimming.

For simplicity and clarity of illustration, reference numerals may be repeated among the figures to indicate corresponding or analogous elements. Numerous details are set forth to provide an understanding of the examples described herein. The examples may be practiced without these details. In other instances, well-known methods, procedures, and components are not described in detail to avoid obscuring the examples described. The description is not to be considered as limited to the scope of the examples described herein.

Figure 1:
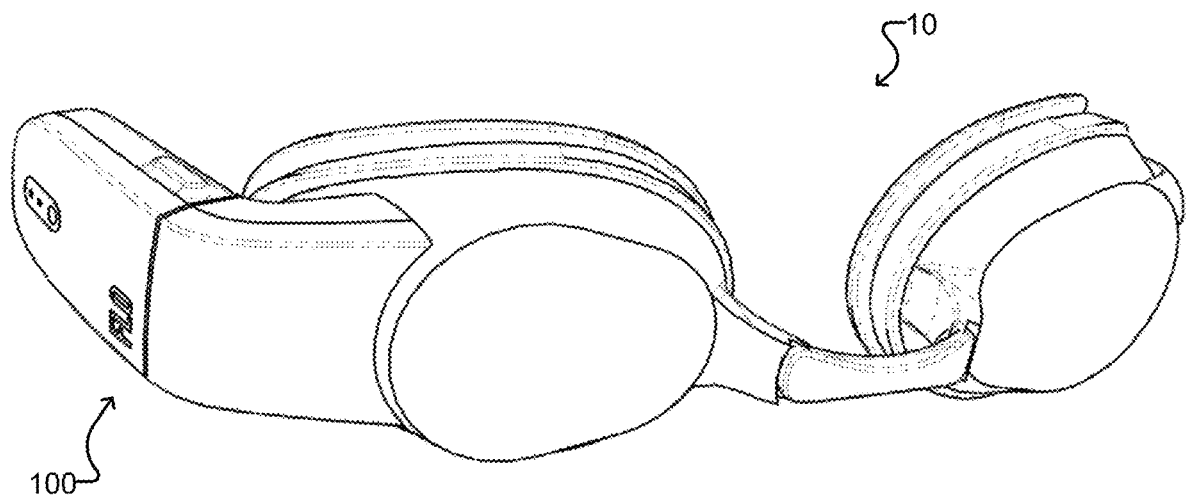
FIG. 1 shows an example embodiment of a wearable device with an electronic system for turn detection.
Figure 2:
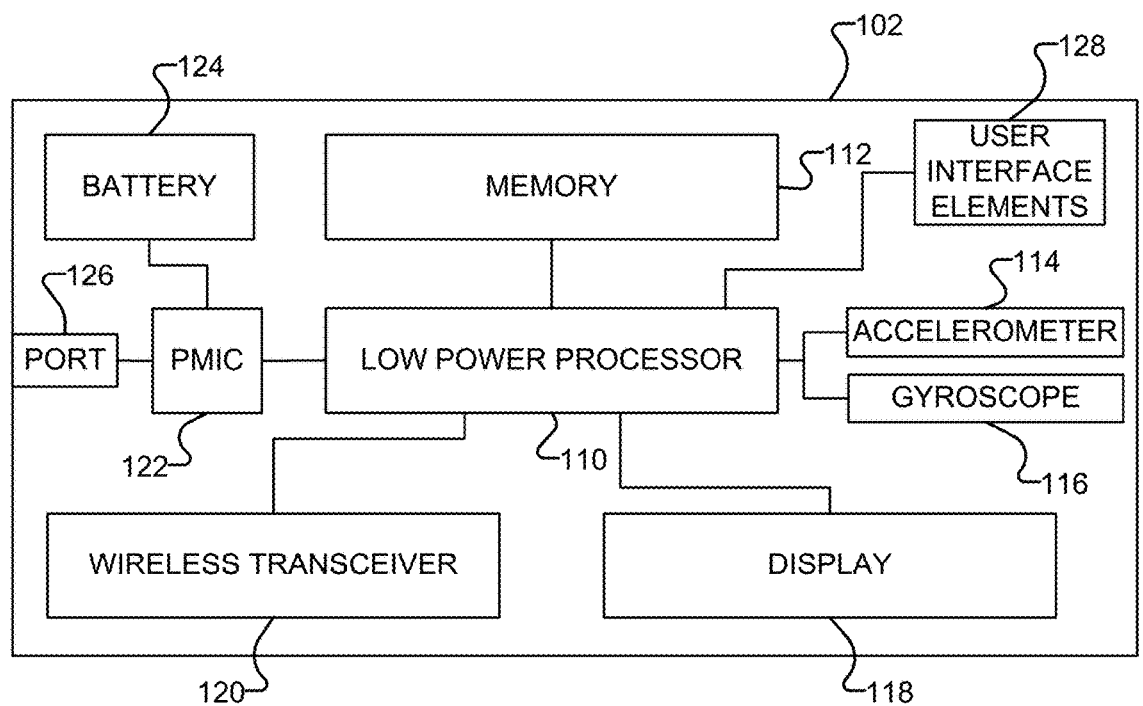
FIG. 2 is a schematic block diagram of an example electronic system for turn detection according to the present disclosure.

FIG. 1 shows an example wearable device in the form of goggles 10 with a system for automatic turn detection and stroke rate detection. FIG. 2 schematically illustrates elements of an electronic system 100 according to some embodiments of the present disclosure. The electronic system 100 may be incorporated into a wearable device, such as the goggles 10 shown in FIG. 1. Goggles 10 may, for example, comprise goggles with a removable or integrated heads up display (HUD) system as described, for example, in U.S. Provisional Patent Application No. 62/448,516 filed Apr. 21, 2017, which is hereby incorporated herein by reference it its entirety.

The electronic system 100 comprises a low power processor 110, a memory 112, display 118, a wireless transceiver 120, a power management integrated circuit (PMIC) 112, a battery 124, a port interface 126, and one or more switches or other user interface elements 128. The accelerometer 114 and gyroscope 116 measure acceleration and angular velocity, respectively, about a plurality of axes. In some embodiments the accelerometer 114 and gyroscope 116 are each triaxial and configured to measure acceleration and angular velocity, respectively, about three perpendicular axes. The accelerometer 114 and gyroscope 116 provide acceleration and angular velocity signals to the processor 110, which processes these signals by execution of computer readable instructions stored in memory 112 to detect swimming performance metrics such as turns and strokes, as described below.

Turn Detection

Figure 3:
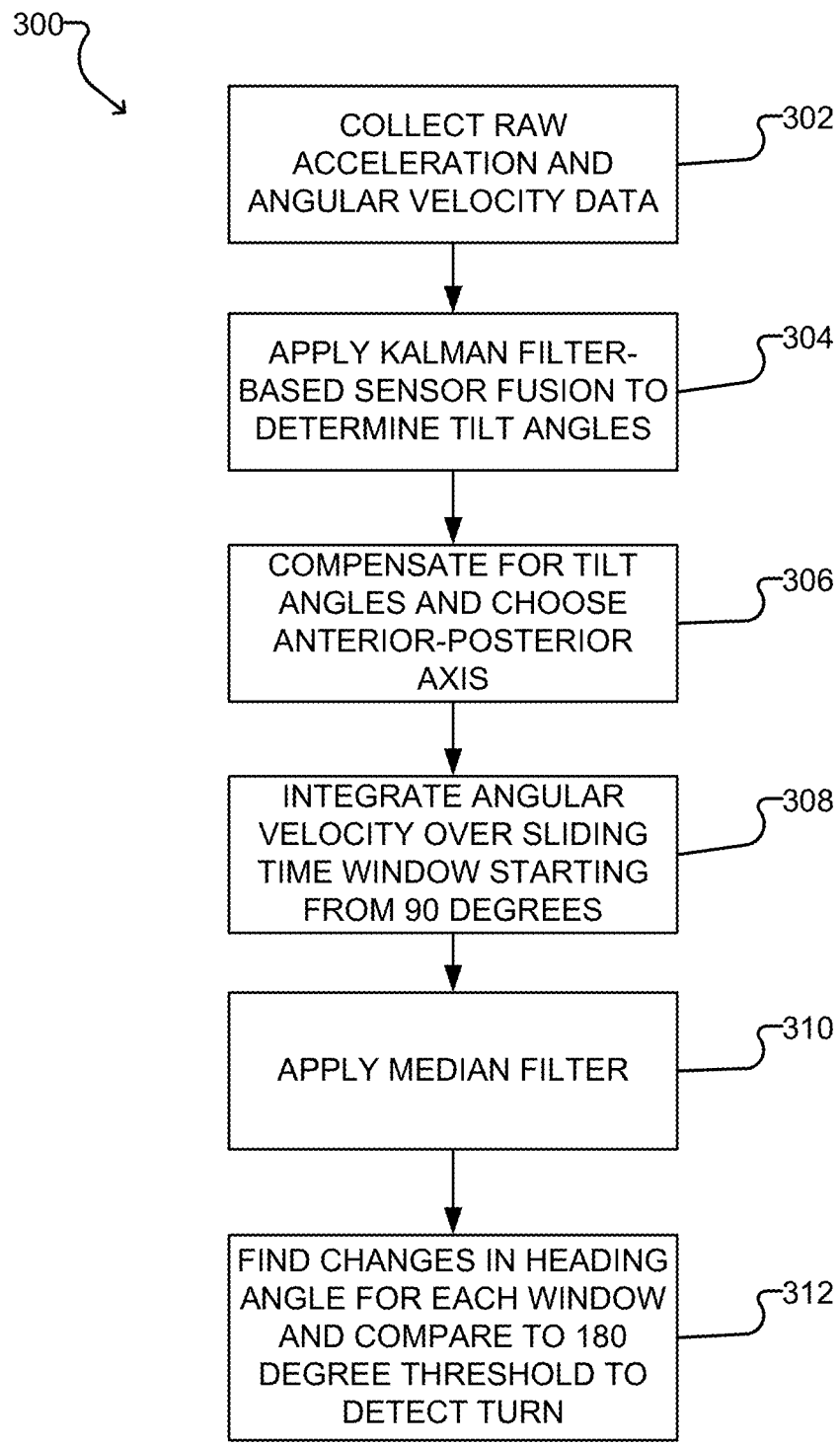
FIG. 3 is a flowchart showing an example method of turn detection according to the present disclosure.

FIG. 3 shows a flowchart of one embodiment of a method 300 for turn detection. Method 300 may be executed by a processor of a head mounted electronic system, such as for example processor 110 of FIG. 2. In block 302, raw acceleration and angular velocity data are collected from a wearable device. The data may be collected continuously in some embodiments. As used herein with respect to collecting data, the term "continuously" means that data is collected by repeatedly sampling the sensors 114/116 at a desired sampling rate. In some embodiments the sampling rate is about 100 Hz. The raw data is then filtered, in some embodiments using a second order Butterworth filter with cutoff frequency of 10 Hz.

In block 304, raw acceleration and angular velocity data are used in a Kalman filter-based sensor fusion algorithm to estimate the roll and pitch angles (a.k.a tilt angles), as disclosed in J. K. Lee, E. J. Park and S. N. Robinovitch, "Estimation of Attitude and External Acceleration Using Inertial Sensor Measurement During Various Dynamic Conditions," in *IEEE Transactions on Instrumentation and Measurement*, vol. 61, no. 8, pp. 2262-2273, August 2012. Roll angle is defined as rotation of swimmer's body around the superior-interior (or longitudinal) axis. Pitch angle is defined as the rotation around the mediolateral axis. Heading angle is defined as the rotation around the anterior-posterior axis. In this fused tilt angle estimation method, the gyroscope captures the dynamic changes in tilt angles whereas the accelerometer limits the integration drift of angular velocity. As a result, the estimated tilt angle remains accurate and drift-free during dynamic motion (e.g. in swimming).

In block 306, the estimated tilt angles are used to compensate the triaxial gyroscope's orientation. A rotation matrix is calculated using the tilt angles and the rotation matrix is then applied to align two axes of gyroscope within a horizontal plane. As a result of this compensation, two axes of the gyroscope data will be orientated in a horizontal plane with the third one perpendicular to the horizontal plane (i.e. vertical) and parallel to the anterior-posterior axis of swimmer's body.

In block 308, gyroscope data about the anterior-posterior axis is integrated over a sliding time window in order to calculate the changes in swimmer's heading angle over the window. In some embodiments, each time window is approximately 6 s long, and the windows overlap by at least 50%. For example, in some embodiments a new 6s window starts every 1.75 s, such that each window overlaps with a preceding window by about 70%.

Since the heading angle (which shows the direction of swimming) is a periodic function in the range of 0 to 360 degrees, when the heading angle value is close to its upper and lower limits, a small change in swimmer's direction will result in large fluctuations in heading angle. This can subsequently satisfy the turn detection criteria and result in a false positive in certain prior art turn detection methods.

Figure 4:
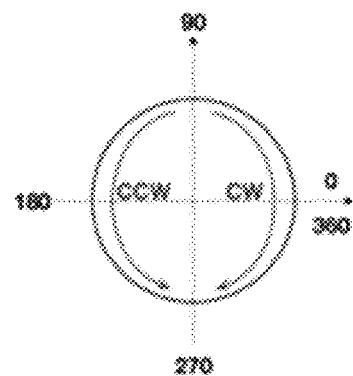
FIG. 4 illustrates heading angle variations for a clockwise and a counterclockwise turn where the heading is initialized at 90°.
Figure 5:
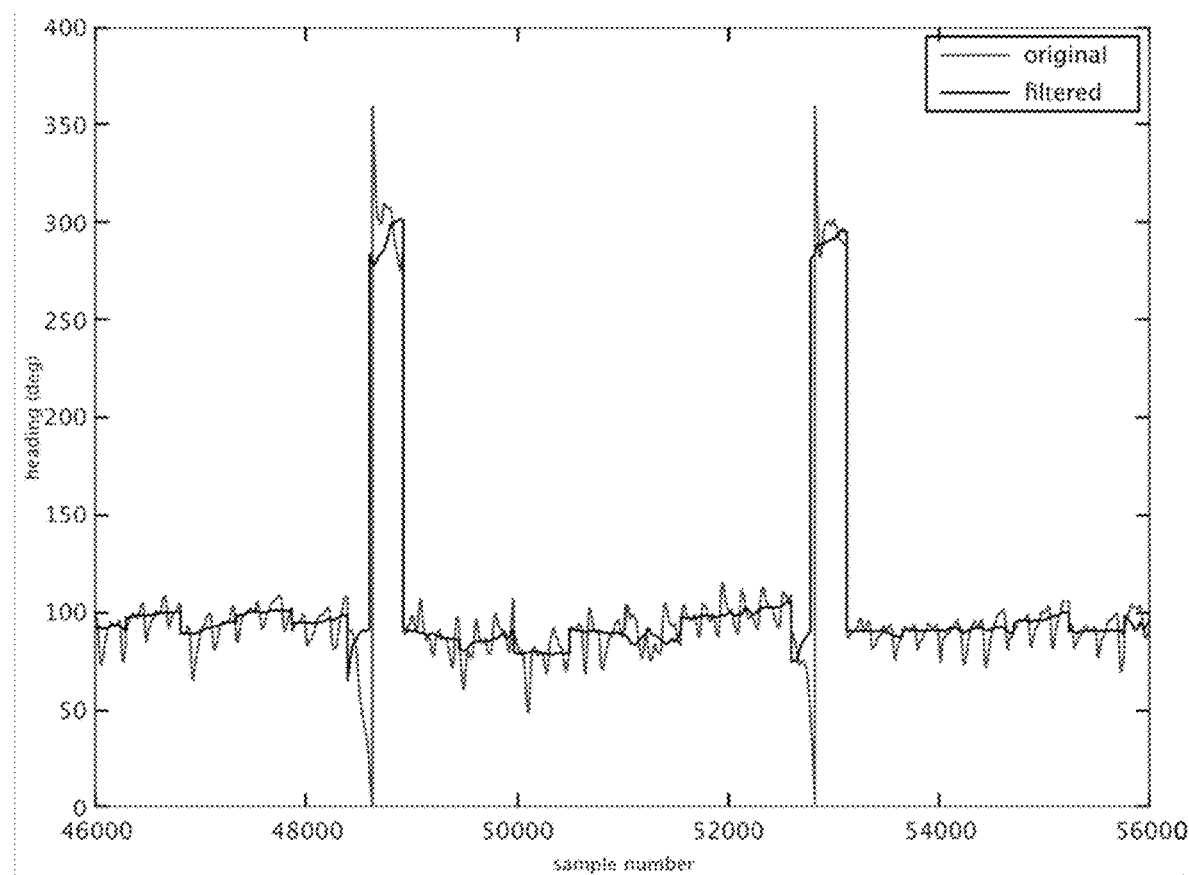
FIG. 5 illustrates heading angle variation over two turns and the effect of filtering.
Figure 6:
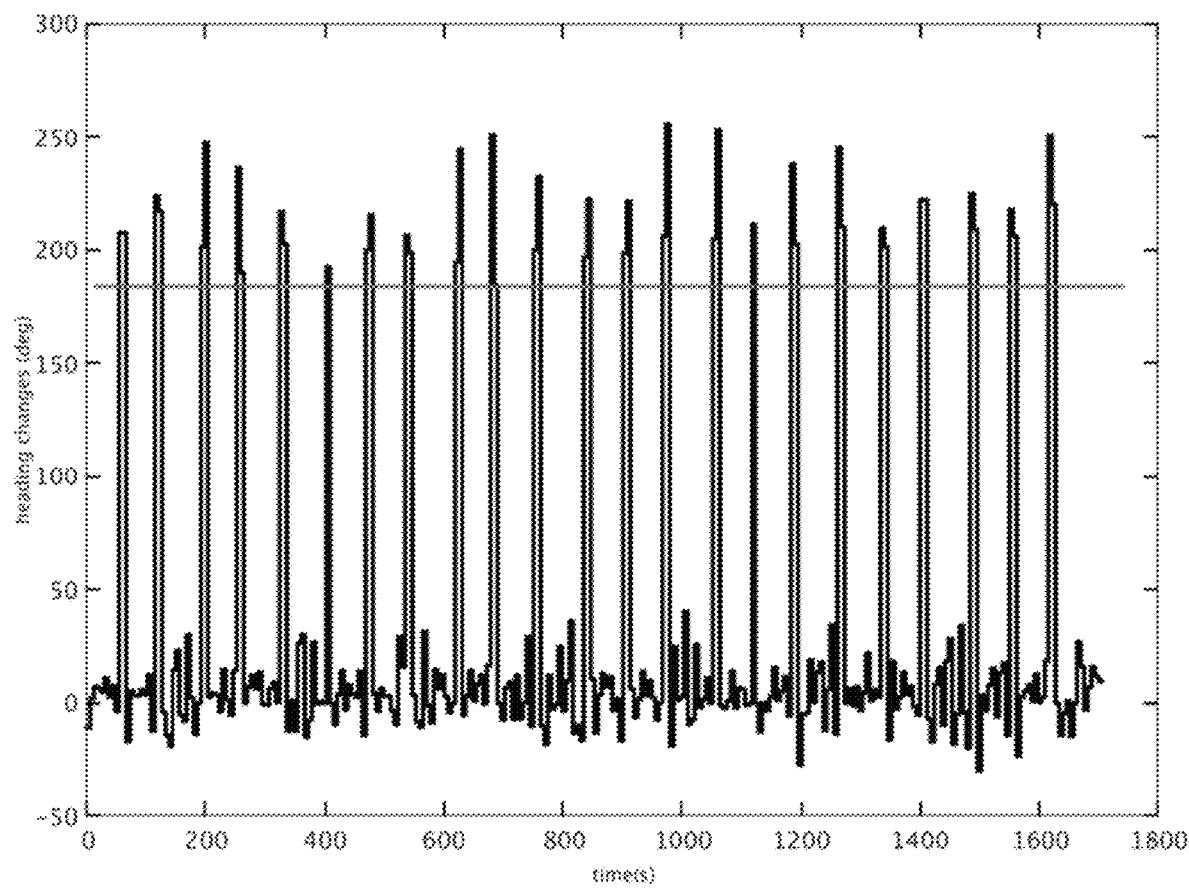
FIG. 6 illustrates heading angle variation during a 24 pool-length swim.

To avoid heading fluctuations that happen when the heading angle is close to 0 or 360 degree, at the start of each window, the heading angle is initialized at a non-zero angle. In some embodiments the heading angle is initialized at about 90 degrees, as shown for example in FIG. 4 (or at about 270 degrees in other embodiments). The heading angle may be initialized at angles other than about 90 or 270 degrees, however, due to head movements around the anterior-posterior axis in swimming (e.g. breathing in freestyle) large heading variations of about 60 degrees might happen during strokes. Initializing the heading angle at around 90 (or 270 degrees will make sure that even large heading fluctuations during strokes won't get close to 0 or 360 degrees. Additionally, initialization at about 90 degrees will make sure that the final heading angle at the end the turn (regardless of the turning direction) will be consistently around 270 degrees (and far from 0 or 360 degrees). In terms of consistency, due to periodicity of heading angle, it is expected that an initial angle of around 270 degrees will give similar results as the initial angle of around 90 degrees. On the other hand, an initial heading angle of around 180 degree (depending on the turn direction and the amount of change in the heading during the turn), might results in the heading angle fluctuation between 0 and 360 degree at the end of the turn. This will result in inconsistent peaks compared to the initial angle of around 90 (or 270) degrees. It is assumed that swimmer's heading will remain almost constant during each lap except for the turn duration where a large change in the heading angle is expected. By initializing the heading angle at 90 (or 270) degrees, relatively small changes in heading angle which might happen during different strokes (excluding turns) won't result in high fluctuations the estimated heading angle. It is expected that each turn will result in about 180 degree change in swimmer's heading angle, as shown for example in FIG. 5 and FIG. 6. Since the windows are short, the amount of heading angle drift caused by integration of gyroscopes' time-varying bias is assumed to be small compared to the changes that happen during a turn.

To make sure that a full turn is captured in the 6 s window, at least a 50% overlap is used between each window in some embodiments.

In block 310, the calculated heading angle over each 6 s window is then median filtered. Looking at FIG. 4, it can be seen that a turn in counterclockwise direction will result in smooth change of heading angle from 90 degrees to about 270 degrees. In this case the median filtered heading angle will also smoothly follow this change. On the other hand, a turn in clockwise direction, will result in the following changes in the heading angle: a change from 90 degrees to 0 degrees, then a jump from 0 degree to 360 degrees, followed by a change from 360 degree to about 270 degrees. In this case, the median filter removes the fluctuations in the middle (fluctuation between 0 to 360 degrees) resulting in a smooth change from 90 degrees to 270 degrees. An example of this can be seen in FIG. 5.

In block 312, for each 6 s window, the amount of change in filtered heading angle (which is equal to the maximum heading angle in the window minus the minimum heading angle in the window) is calculated. Then, this change is compared to the threshold value of approximately 180 degrees. In some embodiments, a threshold of slightly less than 180 degrees (e.g. 175) is used to avoid false negatives where a swimmer does not come out of a turn straight. If the change in heading angle is higher than this threshold value, then a turn is detected for that window. Due to the overlap between the windows, one turn might be detected in multiple successive windows. Thus, regardless of the number of these successive windows in which a turn is detected, the proposed method considers all of them as a single turn.

Figure 7:
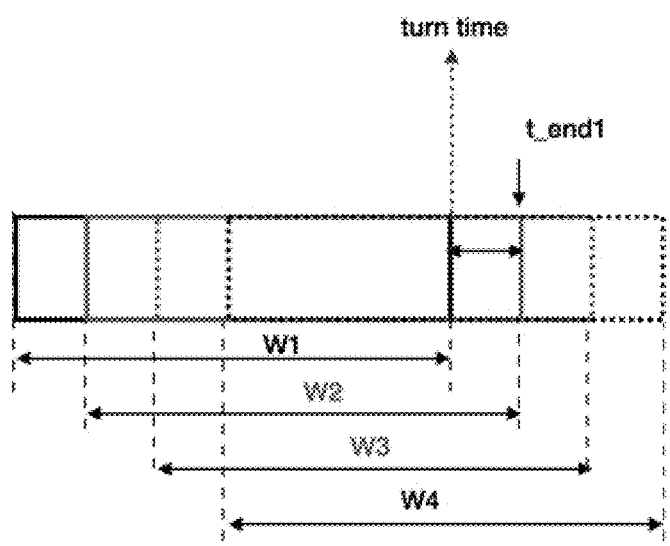
FIG. 7 illustrates four overlapping time windows of a turn detection method according to an example embodiment.

Once a turn is detected, then turn time will be determined. FIG. 7 shows an example of successive windows W1-W4, where turns are detected in windows W2 and W3. To determine the turn time, in some embodiments the method finds the timestamp of the end of the first window where turn is detected (t_end1 of W2 in FIG. 7), and registers the turn time as the timestamp of the end of its preceding window (turn time at end of W1 in FIG. 7). In other embodiments, more accurate turn time information can be obtained by finding the acceleration peak during the windows in which a turn is detected that corresponds to the moment where wall push-off happens. Once turn time is calculated, swimming speed can be derived by knowing the duration between two successive turns and pool length. Additionally, once a turn is registered swim distance will be updated based on the pool length.

Stroke Rate Detection

Figure 8:
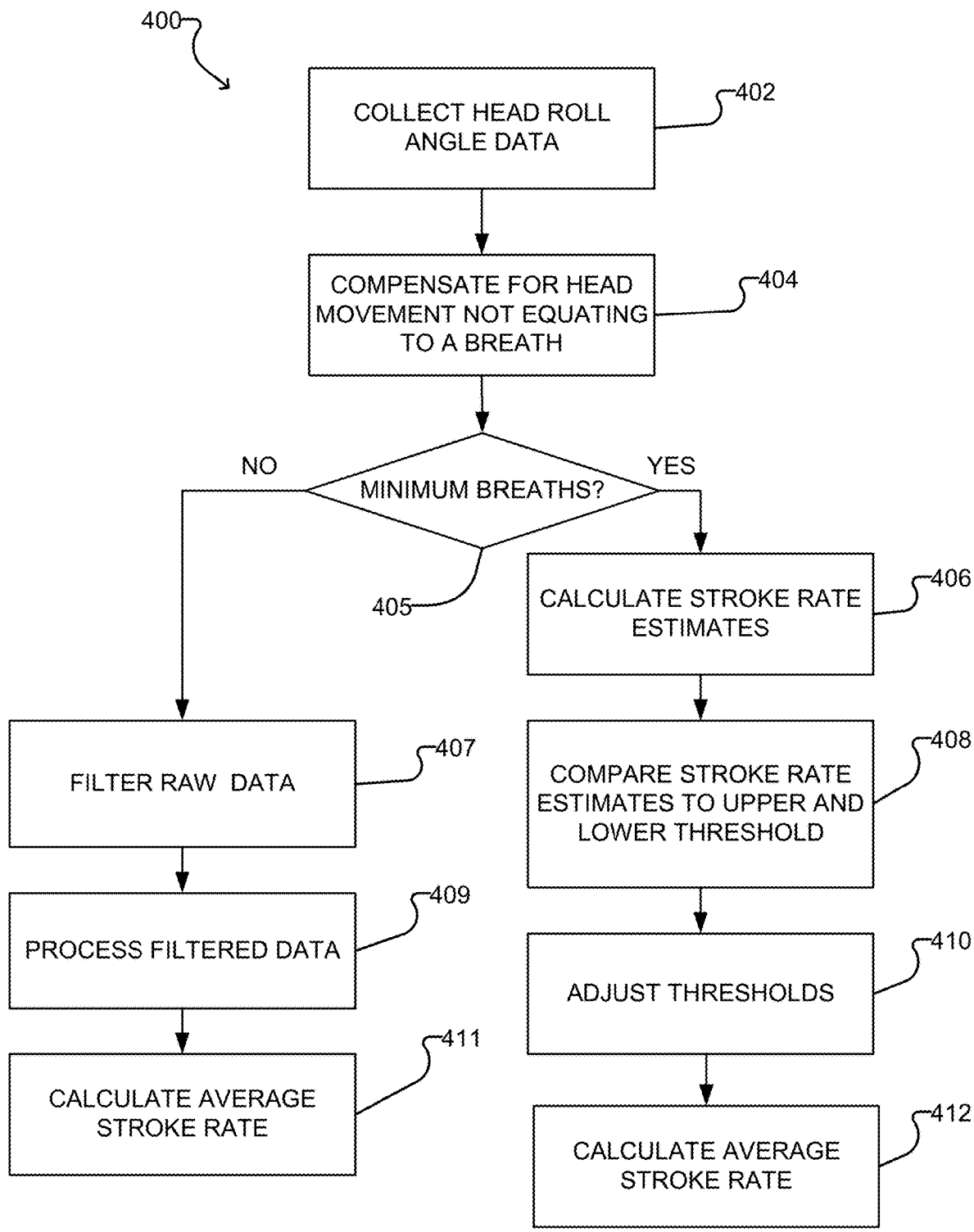
FIG. 8 is a flowchart showing an example method of stroke rate detection for freestyle according to the present disclosure.
Figure 12:
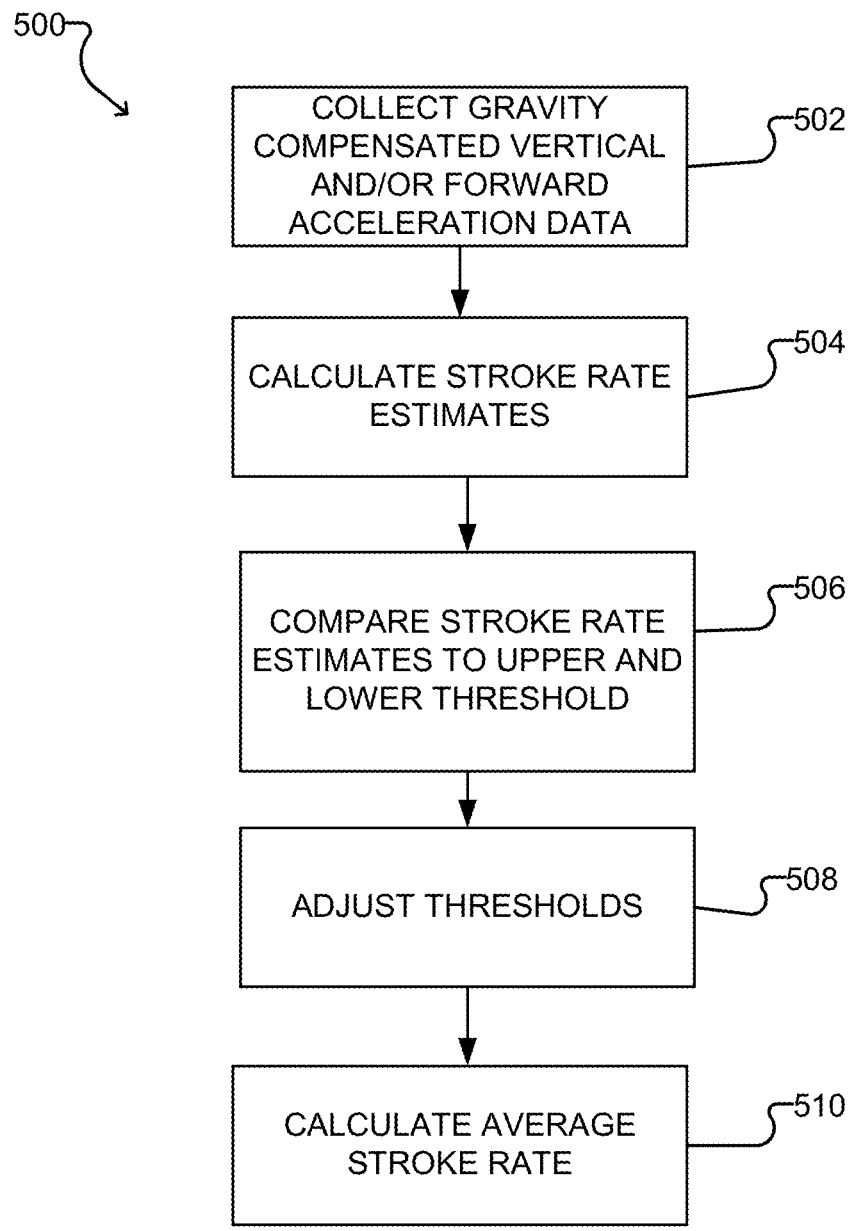
FIG. 12 is a flowchart showing an example method of stroke rate detection for breaststroke and butterfly according to the present disclosure.

A head-mounted electronic system with an IMU having a triaxial accelerometer and triaxial gyroscope may also be used for detecting stroke rates. FIGS. 8, 12 and 16 are flowcharts showing steps of example methods for detecting stroke rate for freestyle, butterfly/breaststroke, and backstroke, respectively, and are discussed in detail below.

In some embodiments, the processor of a head-mounted electronic system is configured to automatically determine a stroke type and execute a stroke rate detection method selected according to the determined stroke type. Determining a stroke type may, for example, detecting a stroke profile based on acceleration and rate of turn signals from the IMU and comparing the detected stoke profile to one or more ideal stroke profiles stored in memory. In some embodiments, the processor may be configured to automatically determine a stroke type utilizing machine learning, such as for example support vector machines.

In the example methods discussed below, the processor of a head-mounted electronic system is configured to collect data from the IMU continuously while the user is swimming. In some embodiments, the processor of a head-mounted electronic system is configured to determine a stroke rate for the detected stroke type after each detected turn (e.g., determine the stroke rate after completion of a full length of the pool). In other embodiments, the processor of a head-mounted electronic system is configured to determine a stroke rate for the detected stroke type at other times or intervals, such as for example after a predetermined time period, or after detecting at least 3 breathing instances.

Freestyle

In freestyle, swimmers turn their head to left or right for breathing. Thus, when a head-mounted IMU is used, breathing can be accurately detected using the peaks in head roll angle. The head roll angle may, for example, be determined from raw acceleration and angular velocity data as described above.

An example stroke rate detection method disclosed herein uses head roll angle to detect breathing instances and then finds the number of strokes in between two successive breathing instances. Assuming that roll angle signal is available for 1 full length of freestyle, the stroke rate detection method follows the steps shown in FIG. 8.

Figure 9:
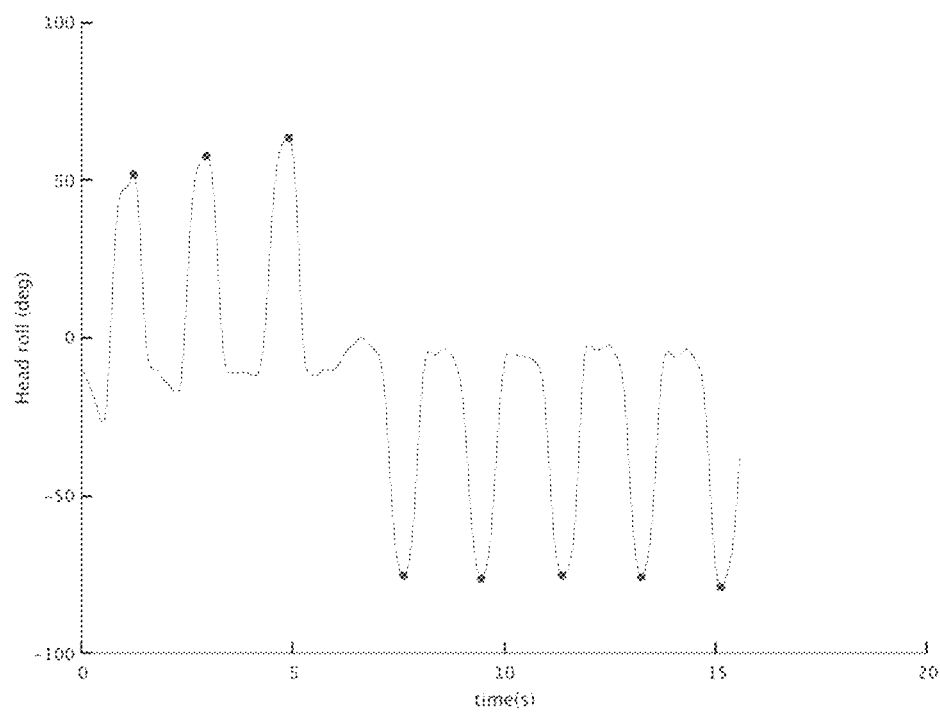
FIG. 9 is a graph showing head roll angle over time for a sample breathing pattern during one length of freestyle.

FIG. 8 shows a flowchart of one embodiment of a method 400 for freestyle stroke rate determination. In block 402, head roll angle data is collected (e.g. by collecting raw acceleration and angular velocity data and applying a Kalman filter-based sensor fusion algorithm as described above). In some embodiments, for each swimming length, all negative and positive peaks in roll angle (which correspond to breathing on the right and left side respectively) with threshold value of at least 45 degrees (the roll angle is 0 when swimmers' look down) are found and the amplitude and timestamp for each peak are saved. FIG. 9 is a graph showing head roll angle over time for a sample breathing pattern during one length of freestyle, consisting of 3 breaths on the left and 5 breaths on the right side. The dots show the detected peaks which correspond to each breath.

Figure 10:
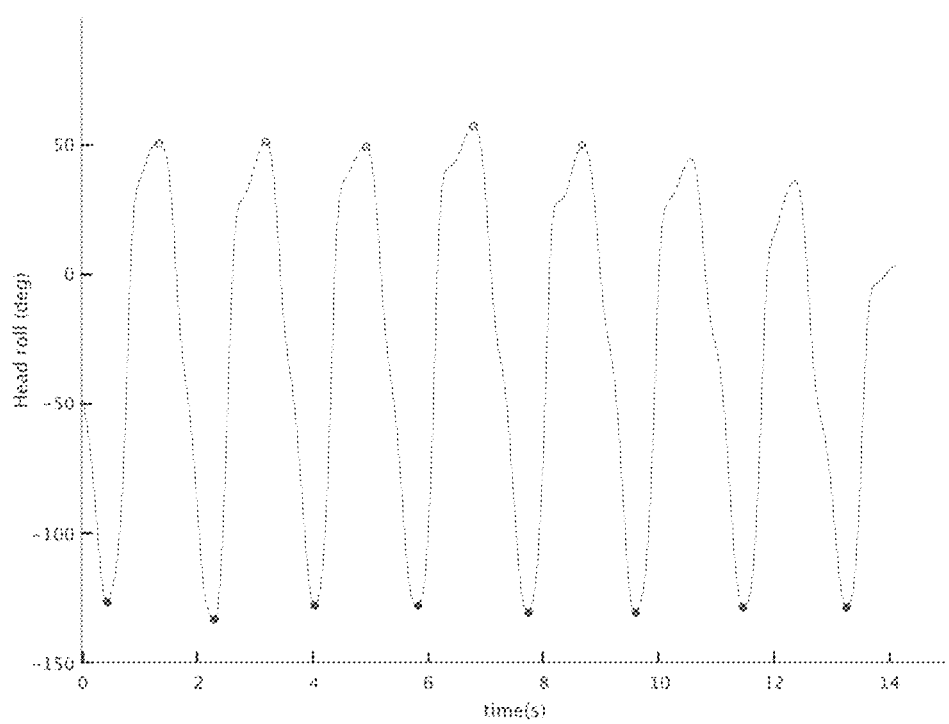
FIG. 10 is a graph showing head roll angle over time for a sample where only the negative peaks correspond to breathing instances.

In block 404, the head roll angle data is compensated for turns of the head not equating to a breath to determine breathing instances. Some swimmers tend to slightly turn their head at each stroke even when they do not breathe. As a result, for such swimmers successive peaks of opposite signs will be detected using the peak detection method described above. However, in these cases, the detected peaks that correspond to breaths have larger absolute amplitude compared to the other peaks. To identify such peaks, at block 404 the average absolute amplitude of positive and negative peaks are compared. If the difference between the average absolute amplitude of the positive and negative peaks is larger than a preset threshold the ones with smaller average absolute amplitude will be ignored. In some embodiments, the threshold difference for ignoring either positive or negative peaks is set to 40 degrees based on the experimental data. FIG. 10 is a graph showing head roll angle over time for a sample where only the negative peaks correspond to breathing instances. As seen in FIG. 10, the average absolute amplitude of the negative peaks is about 125 degrees and the absolute amplitude for positive peaks is about 50 degrees (i.e., a difference in absolute amplitude of about 75 degrees). In this figure, positive peaks (blue circles) do not correspond to breathing instances, and would be ignored at block 404.

In block 405, the number of breathing instances determined at block 404 is compared to a minimum threshold number. For example, in some embodiments the minimum threshold breathing instances is three. When at least the minimum threshold number of breathing instances are determined (block 405 YES output), the method 400 proceeds to blocks 406, 408, 410 and 412 as discussed below. When less than the minimum threshold number of breathing instances are determined (block 405 NO output), which may occur for example when a swimmer is "sprinting", the method 400 proceeds to blocks 407, 409 and 411 as discussed below.

In block 406, stroke rate estimates are calculated based on the time between the peaks that were not ignored at block 404. If the 2 successive peaks have the same sign (2 successive breaths on the same side), then, there are even number of strokes (2, 4 or 6 strokes) in between the 2 successive peaks. If the 2 successive peaks have opposite signs (2 successive breaths on opposite sides), then there are odd number of strokes (3, 5 or 7 strokes) in between the 2 successive peaks. As a result, 3 candidate stroke rates are calculated for each 2 successive peaks and the numbers construct elements of a 1 by 3 array. The arrays are saved into a stroke rate matrix (a n×3 matrix where n=(number of breathing instances)−1).

Figure 11:
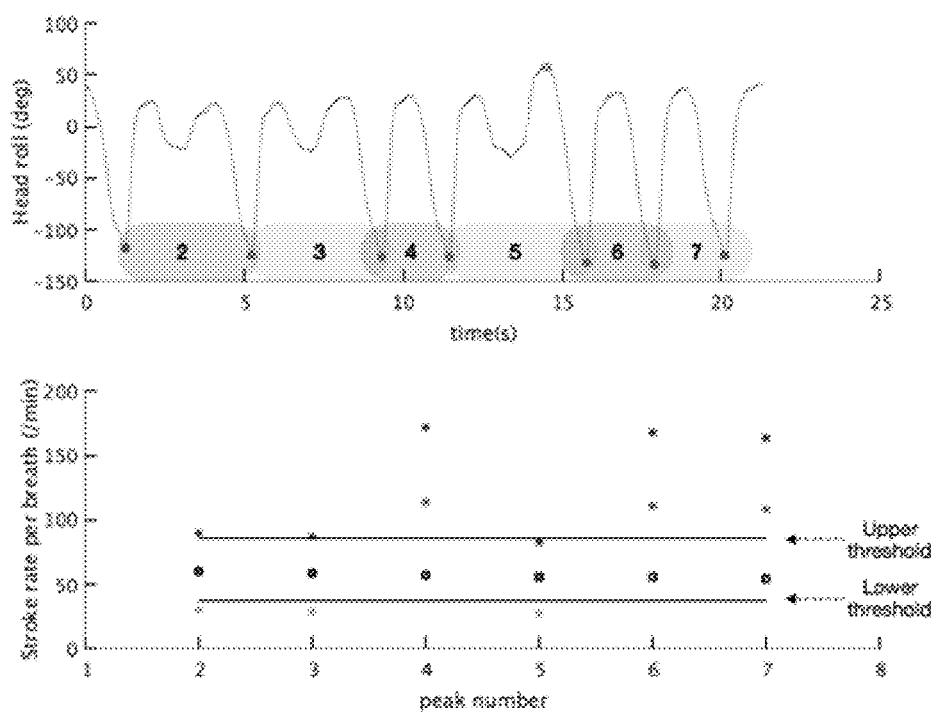
FIG. 11 shows detected breathing instances during 1 full length of freestyle (red dots) in the top graph, and in the bottom graph shows calculated stroke rates in between each 2 successive breathing instances, with the selected ones shown by back circles.

For example, the following stroke rate matrix corresponds to the data shown in FIG. 11:

| 30.162 | 60.324  | 90.486  |
|--------|---------|---------|
| 29.194 | 58.387  | 87.581  |
| 57.232 | 114.463 | 171.695 |
| 27.744 | 55.488  | 83.232  |
| 55.796 | 111.592 | 167.388 |
| 54.306 | 108.613 | 162.919 |

In block 408, the stroke rate estimates are compared to pre-determined thresholds. In some embodiments, the pre-determined thresholds comprise a lower threshold of 38 strokes/minute and an upper threshold of 85 strokes/minute. For each row of the stroke rate matrix, the 3 numbers are compared to preset thresholds to see which candidate stroke rate are within the thresholds. For each row, the numbers that meet the thresholds get selected and the rest are replaced by 0 in the stroke rate matrix.

For example, with these thresholds the above stroke rate matrix is converted to:

| 0      | 60.324 | 0      |
|--------|--------|--------|
| 0      | 58.387 | 0      |
| 57.232 | 0      | 0      |
| 0      | 55.488 | 83.232 |
| 55.796 | 0      | 0      |
| 54.306 | 0      | 0      |

In block 410, the threshold is adaptively tuned to estimate rates. Typical stroke rate of professional swimmers for freestyle is between 40 strokes/min and 70 strokes/min. Thus, it is expected that the preset threshold will cover the stroke rate for most swimmers. However, the following steps may be used to adaptively tune the threshold in case the preset threshold is not high enough. The number of rows in the stroke rate matrix with all zero elements (#zero) is counted and the ratio of #zero/n is calculated. If this ratio is higher than 20% then the upper stroke rate threshold is increased by 5 and the method returns to block 408. This will be repeated for maximum 4 times (or the maximum upper threshold value of 105 strokes/min). FIG. 11 (top) shows detected breathing instances during 1 full length of freestyle (red dots). FIG. 11 (bottom) shows calculated stroke rates in between each 2 successive breathing instances, and the selected ones shown by black circles. For peaks 2, 3 and 5, there are four strokes in between the breathing instances. For peaks 4, 6 and 7, there are two strokes in between the breathing instances.

In block 412, multiple estimates are eliminated and an average stroke rate is calculated. Based on the experimental data from 20 swimmers, after the stroke rate estimates have been compared to the threshold stroke rates, the rows of the stroke rate matrix have either 1 or 2 non-zero elements. At this step, the algorithm extracts the rows with only 1 non-zero value and finds the average stroke rate value. Then for each row with 2 non-zero values, the algorithm chooses the stroke rate value that is closer to the previously calculated average stroke rate value. This selection process is shown in FIG. 11. The bottom plot shows the 3 calculated stroke rate values in between each 2 successive peaks of the top figure. At the end, this step of the algorithm calculates the updated average stroke rate value (e.g., with the selected values from rows with 2 non-zero values being given equal weight to the values from the rows with 1 non-zero value) and reports that as the average stroke rate for the length.

In block 407 the raw head roll angle data is filtered. Considering that the stroke rate for freestyle is normally between 35-95 strokes/min, the signal may be bandpass filtered in the frequency range of 0.1 Hz to 2 Hz (equivalent to the stroke rate of about 6 to 120 strokes/min).

In block 409, the filtered head roll angle data is processed, and a fast Fourier transform (FFT) for head roll angle determined. Then, normalized FFT components (with respect to its highest magnitude) are calculated.

In block 411, the average stroke rate is calculated. The peak of the FFT magnitude spectrum from the head roll angle data is found and is used as the average stroke rate for the length (e.g., the stoke rate with the highest peak in the FFT spectrum). In some embodiments, the stroke rate may be adjusted to experimental results, described further below.

Breaststroke and Butterfly

Figure 13:
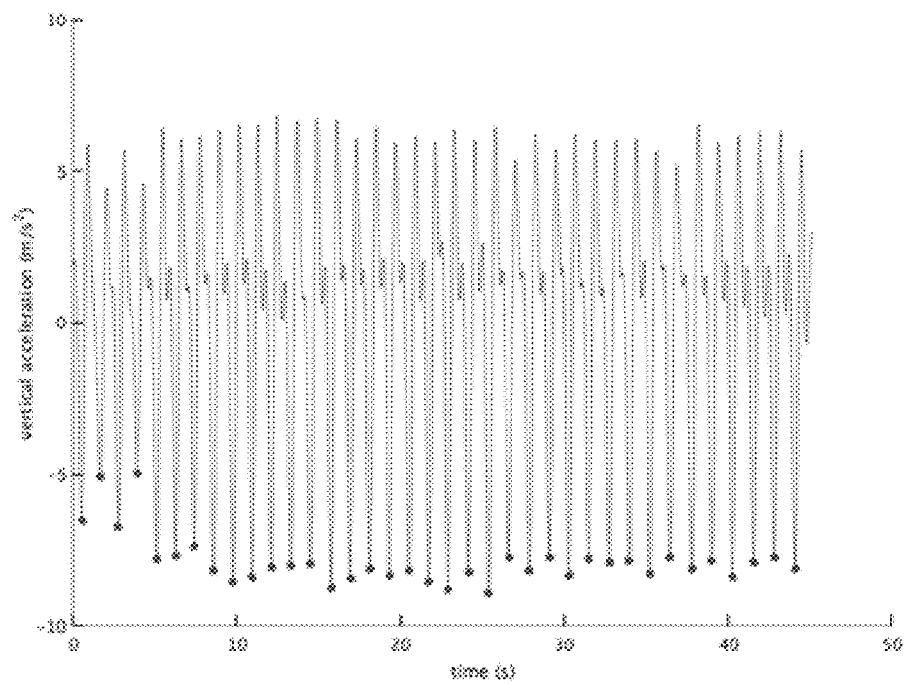
FIG. 13 is a graph showing vertical acceleration over time for sample data, with detected peaks indicated by dots, during 1 length of butterfly.

FIG. 12 shows a flowchart of one embodiment of a method 500 for breaststroke and butterfly stroke rate determination. In block 502, gravity compensated vertical and/or forward acceleration data is collected and peaks identified. In butterfly and breaststroke, at each stroke, there will be a downward and/or forward acceleration that can be captured on a head-mounted IMU. Thus, a gravity-compensated vertical and/or forward acceleration can potentially capture each stroke. For vertical acceleration, all negative peaks below the threshold value of −2.5 $m/s^2$ are found and the timestamp for each peak is saved. For forward acceleration, all peaks above the threshold value of 1 $m/s^2$ are found and the timestamp for each peak is saved. These peaks correspond to strong downward motion. FIG. 13 is a graph showing vertical acceleration over time for sample data, with detected peaks indicated by dots, during 1 length of butterfly.

In block 504, stroke rate estimates are calculated based on the time between the peaks. Based on experimental data for butterfly, the absolute magnitude of the peaks for non-breathing strokes are smaller than the one for breathing strokes. Thus, some of the non-breathing butterfly strokes might be missed by relying only on the threshold for peak detection in block 502 above. For butterfly, swimmers typically breathe at every stroke, at every 2 strokes or at every 3 strokes. As a result, 3 candidate stroke rates are calculated for each 2 successive peaks and the numbers construct elements of a 1 by 3 array. The arrays are saved into a stroke rate matrix (a n by 3 matrix where n=(number of breathing peaks)−1). For example, the following stroke rate matrix corresponds to the data shown in FIG. 14:

| | | |
|---:|---:|---:|
| 38.909 | 77.818 | 116.727 |
| 13.148 | 26.297 | 39.445 |
| 44.276 | 88.552 | 132.828 |
| 38.143 | 76.286 | 114.429 |

In block 506, the stroke rate estimates are compared to pre-determined thresholds. For each row of the stroke rate matrix, the 3 numbers are compared to the preset threshold to see which candidate stroke rate meet the threshold. For each row, the numbers that meet the threshold get selected and the rest are replaced by 0 in the stroke rate matrix. Experiments suggest the initial lower threshold and upper threshold for stroke rate should be set to 17 strokes/min and to 37 strokes/min respectively.

In block 508, the threshold is adaptively tuned to estimate rates. Typical stroke rate of professional swimmers for butterfly and breast stroke is less than 60 strokes/minute. Thus, the following steps may be implemented at block 508 to adaptively tune the threshold in case the preset threshold is not high enough. The number of rows in the stroke rate matrix with all zero elements (#zero) will be counted and the ratio of #zero/n is calculated. If this ratio is higher than 20% then the upper stroke rate threshold is increased by 5 and the method returns to block 506. This will be repeated for maximum 5 times (or the maximum upper threshold value of 62 strokes/min). Based on the experimental data from 20 swimmers, after the stroke rate estimates have been compared to the threshold stroke rates, the rows of the stroke rate matrix have either 1 or 2 non-zero elements. At this step, the algorithm extracts the rows with only one non-zero value and finds the average stroke rate value. Then, for each row with two non-zero values, the algorithm chooses the stroke rate value that is closer to the previously calculated average stroke rate value.

FIG. 14 (top) shows detected peaks of vertical acceleration during 1 full length of butterfly. FIG. 14 (bottom) shows 3 calculated stroke rates in between each 2 successive breathing instances, and the selected ones shown by back circles. For peaks 2, 4 and 5, there is only 1 stroke in between the successive detected peaks. For peak 3, there are 3 strokes in between the successive detected peaks. At the end, the algorithm calculates the updated average stroke rate value and reports that as the average stroke rate for the length.

FIG. 15 shows the result of the same stroke rate detection method for breaststroke. Since in breaststroke all strokes include breathing, as can be seen in FIG. 15, the method selects the first element in each row of the stroke rate matrix which correspond to only 1 stroke in between each 2 successive peaks. Thus the first element in each row of the stroke rate matrix for breaststroke will always be selected, unless a peak is missed (e.g. due to measurement error) in which case the second value would be selected.

Backstroke

FIG. 16 shows a flowchart of one embodiment of a method 600 for backstroke stroke rate determination. In block 602, gravity compensated vertical acceleration data, forward acceleration data and/or head roll angle data is collected. In backstroke, at each stroke there is downward head movement that can be captured using the gravity-compensated vertical acceleration signal. Additionally, at each stroke there is forward acceleration (along the longitudinal axis of swimmer's body) that can be captured on a head-mounted IMU. Furthermore, some swimmers turn their head to the left and right with each stroke, and such movement can be captured using head roll angle data.

In block 604, the raw gravity compensated vertical acceleration data, forward acceleration data and/or head roll angle data is filtered. Considering that the stroke rate for backstroke is normally between 40-90 strokes/min, the three signals may be bandpass filtered in the frequency range of 0.1 Hz to 2 Hz (equivalent to the stroke rate of about 6 to 120 strokes/min).

In block 606, the filtered gravity compensated vertical acceleration data, forward acceleration data and/or head roll angle data is processed, and a fast Fourier transform (FFT) for each of the vertical and forward acceleration is determined. Then, for each signal, normalized FFT components (with respect to its highest magnitude) are calculated.

In block 608, the peaks of the normalized FFT for the vertical acceleration data, forward acceleration data and/or head roll angle data are compared and one selected. Depending on the swimmer's backstroke technique, one or more of the vertical acceleration data, forward acceleration data and head roll angle data result in a dominant peak around the stroke frequency. To choose which of the three signals better represents the stroke rate of the swimmer, average of the normalized FFT components' magnitude is calculated, and the signal with the lowest average FFT component value is selected. Since the FFT components are all normalized, the one with the lowest average value may have a more dominant peak.

As it can be seen in the FIGS. 17-19, in the case that there are multiple peaks in the FFT components, the average value of FFT components' magnitude is higher. Thus, the signal with smaller average FFT value is chosen for further processing. FIG. 17 shows normalized FFT spectrum for a swimmer where the peak of FFT signal is more dominant for the vertical acceleration compared to forward acceleration. The solid line shows the average value, which is lower for vertical acceleration, so vertical acceleration signals are chosen.

FIG. 18 shows normalized FFT spectrum for a swimmer where the peak of FFT signal is more dominant for the forward acceleration compared to vertical acceleration. The solid line shows the average value, which is lower for forward acceleration, so forward acceleration signals are chosen.

FIG. 19 shows normalized FFT spectrum for a swimmer where the peak of FFT signal has only one dominant peak in both the vertical acceleration and the forward acceleration. The solid line shows the average value, which is lower for vertical acceleration, so vertical acceleration signals are chosen.

In block 610, the average stroke rate is calculated. The peak of the FFT magnitude spectrum (from one or more of the vertical acceleration data, the forward acceleration data and the head roll angle data) is found and is used as the average stroke rate for the length (e.g., the stoke rate with the highest peak in the selected FFT spectrum). In some embodiments the stroke rate may be adjusted to experimental results, described further below.

In experiments, the calculated stroke rate was compared to the benchmark stroke rate data obtained from video analysis. The experimental data consists of 80 lengths of backstroke from 20 swimmers. FIG. 20 shows the calculated stroke rate values (red dots) versus the reference values (black dots). The calculated stroke rate captures the trend in the reference stroke rate. However, in all cases, the calculated stroke rate overestimates the actual stroke rate, meaning that frequency of head forward/vertical acceleration is higher than the stroke rate. This means that there might be more than 1 phase in each stroke that cause fluctuation in forward and/or vertical acceleration on the head. As a result, a mapping was done to find the actual stroke rate. To solve this overestimation problem, coefficients of the best linear fit (y=a*x+b) between the estimated stroke rate and reference stroke rate are found (based on the collected data from 20 swimmers on 80 laps). Then, a corrected stroke rate can be calculated using the linear coefficients. Experiments suggest the following formula improves the estimation of stroke rate: corrected_rate=0.86*estimated_rate+0.52. FIG. 21 shows the corrected stroke rate values (blue dots) after applying the above mentioned linear correction.

Experimental Data from Prototype Embodiment

Each of the above methods for stroke rate determination were examined based on the collected data from 20 swimmers, swimming 4 lengths of each stroke type (80 length in total for each stroke type). The following table shows the mean absolute error (MAE) and the mean absolute percentage error (MAPE) of estimated stroke rate calculated for each stroke. This table also shows the correlation coefficient between the estimated and the benchmark stroke rate.

|  | MAE (strokes/min) | MAPE (%) | Correlation coefficient |
| --- | --- | --- | --- |
| Freestyle | 1.77 ± 1.67 | 2.85 ± 2.74 | 0.962 |
| Butterfly | 1.49 ± 1.45 | 4.00 ± 4.34 | 0.958 |
| Breaststroke | 0.66 ± 0.71 | 2.05 ± 2.25 | 0.982 |
| Backstroke | 2.30 ± 2.27 | 3.93 ± 3.59 | 0.948 |

The swim sessions are video recorded and benchmark stroke rate data is extracted from the video recordings. FIG. 22 shows the box plot of errors for each stroke type. Based on the table above and FIG. 22, the stroke rate estimation error is better than about 10% for almost all cases (excluding the outlier points) and better than about 3% for more than 50% of the dataset (the data in between first and third quartiles). Based on FIG. 22, stroke rate estimation error is very similar for freestyle, backstroke and butterfly. However, the estimated stroke rate is relatively more accurate for breaststroke compared to the other 3 strokes. This is due to the fact that in breaststroke, every single stroke includes a very distinct head movement pattern (up and down movement) whereas in the other 3 strokes the developed algorithms indirectly capture the effect of each stroke on head movements.

It will be appreciated that numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description is not to be considered as limiting the scope of the embodiments described herein in any way, but rather as merely describing implementation of the various example embodiments described herein.

The description provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

The embodiments of the devices, systems and methods described herein may be implemented in a combination of both hardware and software. These embodiments may be implemented on programmable computers, each computer including at least one processor, a data storage system (including volatile memory or non-volatile memory or other data storage elements or a combination thereof), and at least one communication interface. For example, the programmable computers may be a server, network appliance, set-top box, embedded device, computer expansion module, personal computer, laptop, personal data assistant, cloud computing system or mobile device. A cloud computing system is operable to deliver computing service through shared resources, software and data over a network. Program code is applied to input data to perform the functions described herein and to generate output information. The output information is applied to one or more output devices to generate a discernible effect. In some embodiments, the communication interface may be a network communication interface. In embodiments in which elements are combined, the communication interface may be a software communication interface, such as those for inter-process communication. In still other embodiments, there may be a combination of communication interfaces.

Program code is applied to input data to perform the functions described herein and to generate output information. The output information is applied to one or more output devices. In some embodiments, the communication interface may be a network communication interface. In embodiments in which elements may be combined, the communication interface may be a software communication interface, such as those for inter-process communication. In still other embodiments, there may be a combination of communication interfaces implemented as hardware, software, and combination thereof.

Each program may be implemented in a high level procedural or object oriented programming or scripting language, or both, to communicate with a computer system. However, alternatively the programs may be implemented in assembly or machine language, if desired. In any case, the language may be a compiled or interpreted language. Each such computer program may be stored on a storage media or a device (e.g. ROM or magnetic diskette), readable by a general or special purpose programmable computer, for configuring and operating the computer when the storage media or device is read by the computer to perform the procedures described herein. Embodiments of the system may also be considered to be implemented as a non-transitory computer-readable storage medium, configured with a computer program, where the storage medium so configured causes a computer to operate in a specific and predefined manner to perform the functions described herein.

Furthermore, the system, processes and methods of the described embodiments are capable of being distributed in a computer program product including a physical non-transitory computer readable medium that bears computer usable instructions for one or more processors. The medium may be provided in various forms, including one or more diskettes, compact disks, tapes, chips, magnetic and electronic storage media, and the like. The computer useable instructions may also be in various forms, including compiled and non-compiled code.

Embodiments described herein may relate to various types of computing applications, such as image processing and generation applications, computing resource related applications, speech recognition applications, video processing applications, semiconductor fabrication, and so on. By way of illustrative example embodiments may be described herein in relation to image-related applications.

Throughout the foregoing discussion, numerous references will be made regarding servers, services, interfaces, portals, platforms, or other systems formed from computing devices. It should be appreciated that the use of such terms is deemed to represent one or more computing devices having at least one processor configured to execute software instructions stored on a computer readable tangible, non-transitory medium. For example, a server can include one or more computers operating as a web server, database server, or other type of computer server in a manner to fulfill described roles, responsibilities, or functions.

The technical solution of embodiments may be in the form of a software product. The software product may be stored in a non-volatile or non-transitory storage medium, which can be a compact disk read-only memory (CD-ROM), a USB flash disk, or a removable hard disk. The software product includes a number of instructions that enable a computer device (personal computer, server, or network device) to execute the methods provided by the embodiments.

The embodiments described herein are implemented by physical computer hardware, including computing devices, servers, receivers, transmitters, processors, memory, displays, and networks. The embodiments described herein provide useful physical machines and particularly configured computer hardware arrangements.

Although the embodiments have been described in detail, it should be understood that various changes, substitutions and alterations can be made herein. Moreover, the scope of the present application is not intended to be limited to the particular embodiments of the process, machine, manufacture, composition of matter, means, methods and steps described in the specification. As can be understood, the examples described above and illustrated are intended to be exemplary only.

As will be apparent to those skilled in the art in light of the foregoing disclosure, many alterations and modifications are possible to the methods and systems described herein. While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as may reasonably be inferred by one skilled in the art. The scope of the claims should not be limited by the embodiments set forth in the examples, but should be given the broadest interpretation consistent with the foregoing disclosure.

The present disclosure may be embodied in other specific forms without departing from its spirit or essential characteristics. The described embodiments are to be considered in all respects only as illustrative and not restrictive.

The invention claimed is:

1. A method for detection of swimming turns comprising:
    mounting a wearable device comprising an accelerometer, a gyroscope and a processor on a swimmers head;
    continuously measuring acceleration and angular velocity with the accelerometer and gyroscope to provide acceleration and angular velocity signals to the processor;
    processing the acceleration and angular velocity signals to determine roll and pitch angles;
    applying an axial correction to axes of the gyroscope based on the determined roll and pitch angles to determine corrected angular velocity signals;
    initializing a heading angle at a pre-defined, non-zero value;
    integrating said corrected angular velocity signals over a time window to determine changes to the heading angle;
    determining a maximum heading angle and a minimum heading angle within the time window;
    recording a turn when a difference between the maximum heading angle and the minimum heading angle within the time window is at least approximately 180 degrees;
    automatically detecting a stroke type based on the acceleration and angular velocity signals, wherein automatically detecting the stroke type comprises detecting the stroke type as freestyle;
    continuously measuring head acceleration signals to obtain head roll angle data;
    processing the head roll angle data to determine breath instances;
    when a number of determined breath instances is at least a minimum threshold:
        calculating candidate stroke rate estimates based on time between breath instances;
        comparing the candidate stroke rate estimates to upper and lower threshold values to determine selected stroke rate estimates; and, calculating an average stroke rate from the selected stroke rate estimates;
    and,
    when the number of determined breath instances is lower than the minimum threshold:
        determining a fast Fourier transform (FFT) of the head roll data;
    and,
        processing the head roll angle data to determine an average stroke rate based on a peak value FFT component.

2. The method of claim 1 wherein processing acceleration and angular velocity signals and integrating comprises using a sensor fusion algorithm.

3. The method of claim 1 wherein the pre-defined, non-zero value is about 90 degrees or about 270 degrees.

4. A method for providing a swimmer with real time performance metrics comprising:
    mounting a wearable device comprising a processor and an inertial measurement unit (IMU) comprising an accelerometer and a gyroscope on the swimmers head;
    continuously measuring acceleration and angular velocity with the accelerometer and gyroscope to provide acceleration and angular velocity signals to the processor;
    processing the acceleration and angular velocity signals to determine first roll and pitch angles;
    applying an axial correction to axes of said gyroscope based on said roll and pitch angles to determine corrected angular velocity signals;
    initializing a heading angle at a pre-defined, non-zero value;
    integrating said corrected angular velocity signals over a time window to determine changes to the heading angle;
    determining a maximum heading angle and a minimum heading angle within the time window;
    recording a turn when a difference between the maximum heading angle and the minimum heading angle within the time window is at least approximately 180 degrees;

automatically detecting a stroke type based on the acceleration and angular velocity signals;

when the stroke type is freestyle:
    continuously measuring head acceleration signals to obtain head roll angle data;
    processing the head roll angle data to determine breath instances;
    when a number of determined breath instances is at least a minimum threshold:
        calculating candidate stroke rate estimates based on time between breath instances;
        comparing the candidate stroke rate estimates to upper and lower threshold values to determine selected stroke rate estimates; and,
    calculating an average stroke rate from the selected stroke rate estimates;
and,
    when the number of determined breath instances is lower than the minimum threshold:
        determining a fast Fourier transform (FFT) of the head roll data;
    and,
        processing the head roll angle data to determine an average stroke rate based on a peak value FFT component;

when the stroke type is butterfly or breaststroke:
    continuously measuring head acceleration and angular velocity signals to obtain one or more of compensated vertical acceleration data and forward acceleration data;
    processing the one or more of compensated vertical acceleration data and forward acceleration data to determine breath instances;
    calculating candidate stroke rate estimates based on time between breath instances;
    comparing the candidate stroke rate estimates to upper and lower threshold values to determine selected stroke rate estimates; and
    calculating an average stroke rate from the selected stroke rate estimates;
and,
when the stroke type is backstroke:
    continuously measuring head acceleration and angular velocity signals to obtain one or more of forward acceleration data, compensated vertical acceleration data and head roll angle data;
    determining a fast Fourier Transform (FFT) for each of one or more of forward acceleration data, compensated vertical acceleration data and head roll angle data;
    selecting a more dominant one of one or more of forward acceleration data, compensated vertical acceleration data and head roll angle data having a lowest average of FFT component values; and
    processing the more dominant one of the one or more of forward acceleration data, compensated vertical acceleration data and head roll angle data to determine an average stroke rate based on a peak value FFT component; and
reporting the average stroke rate to the swimmer.

\* \* \* \* \*